(12) United States Patent
Dean et al.

(10) Patent No.: US 8,772,260 B2
(45) Date of Patent: Jul. 8, 2014

(54) METHODS FOR INHIBITING EXPRESSION OF CONNECTIVE TISSUE GROWTH FACTOR

(75) Inventors: Nicholas M. Dean, Encinitas, CA (US); J. Gordon Foulkes, Encinitas, CA (US); Niall O'Donnell, St. Louis, MO (US); C. Frank Bennett, Carlsbad, CA (US); Susan M. Frier, San Diego, CA (US)

(73) Assignees: Isis Pharmaceuticals, Inc, Carlsbad, CA (US); Excaliard Pharmaceuticals, Inc, Carlsbad, CA (US)

( * ) Notice: Subject to any disclaimer, the term of this patent is extended or adjusted under 35 U.S.C. 154(b) by 141 days.

(21) Appl. No.: 13/584,573

(22) Filed: Aug. 13, 2012

(65) Prior Publication Data

US 2013/0190382 A1 Jul. 25, 2013

Related U.S. Application Data

(62) Division of application No. 12/547,474, filed on Aug. 25, 2009, now Pat. No. 8,252,762.

(60) Provisional application No. 61/190,121, filed on Aug. 25, 2008.

(51) Int. Cl.
*A61K 31/70* (2006.01)
*C07H 21/02* (2006.01)
*C07H 21/04* (2006.01)
*C12N 15/113* (2010.01)
*C12Q 1/68* (2006.01)

(52) U.S. Cl.
CPC .......... *C12N 15/113* (2013.01); *C12N 2310/11* (2013.01)
USPC ......... 514/44 A; 435/375; 435/377; 536/23.1; 536/24.1; 536/24.5

(58) Field of Classification Search
None
See application file for complete search history.

(56) References Cited

U.S. PATENT DOCUMENTS

| | | |
|---|---|---|
| 5,585,270 A | 12/1996 | Grotendorst et al. |
| 5,783,187 A | 7/1998 | Grotendorst et al. |
| 5,801,154 A | 9/1998 | Baracchini et al. |
| 5,876,730 A | 3/1999 | Brigstock et al. |
| 5,998,148 A | 12/1999 | Bennett et al. |
| 6,069,006 A | 5/2000 | Grotendorst et al. |
| 6,150,101 A | 11/2000 | Grotendorst et al. |
| 6,232,064 B1 | 5/2001 | Grotendorst et al. |
| 6,358,741 B1 | 3/2002 | Schmidt et al. |
| 6,436,909 B1 | 8/2002 | Dean et al. |
| 6,965,025 B2 | 11/2005 | Gaarde et al. |
| 7,399,845 B2 | 7/2008 | Seth et al. |
| 7,666,853 B2 | 2/2010 | Khvorova et al. |
| 7,709,630 B2 | 5/2010 | Gaarde et al. |
| 7,718,177 B2 | 5/2010 | Grotendorst et al. |
| 7,820,809 B2 | 10/2010 | Khvorova et al. |
| 7,833,989 B2 | 11/2010 | Khvorova et al. |
| 2003/0119010 A1 | 6/2003 | Powell et al. |
| 2003/0153524 A1 | 8/2003 | Hinton et al. |
| 2003/0180300 A1 | 9/2003 | Grotendorst |
| 2003/0180891 A1 | 9/2003 | Young et al. |
| 2004/0259247 A1 | 12/2004 | Tuschl et al. |
| 2005/0059629 A1 | 3/2005 | Gaarde et al. |
| 2005/0136502 A1 | 6/2005 | Riser et al. |
| 2007/0299028 A1 | 12/2007 | Siwkowski et al. |
| 2008/0015114 A1 | 1/2008 | Khvorova et al. |
| 2008/0070856 A1 | 3/2008 | Kreutzer et al. |
| 2008/0108583 A1 | 5/2008 | Feinstein |
| 2008/0119433 A1 | 5/2008 | Tabor |
| 2008/0125352 A1 | 5/2008 | Brigstock et al. |
| 2008/0193443 A1 | 8/2008 | Beskrovnaya et al. |
| 2008/0206256 A1 | 8/2008 | Spong et al. |
| 2009/0069623 A1 | 3/2009 | Oh |
| 2009/0156524 A1 | 6/2009 | Feinstein et al. |
| 2009/0162365 A1 | 6/2009 | Feinstein et al. |
| 2010/0130595 A1 | 5/2010 | Dean et al. |
| 2010/0266532 A1 | 10/2010 | Ferguson |
| 2011/0112168 A1 | 5/2011 | Feinstein et al. |

FOREIGN PATENT DOCUMENTS

| | | |
|---|---|---|
| AU | 2009275387 B2 | 7/2010 |
| EP | 1461352 A2 | 9/2004 |
| EP | 2388318 A1 | 11/2011 |
| GB | 2465902 B | 12/2010 |
| WO | WO 96/38172 A1 | 5/1996 |
| WO | WO 99/66959 A2 | 12/1999 |
| WO | WO 00/13706 A1 | 3/2000 |
| WO | WO 00/27868 A2 | 5/2000 |
| WO | WO 00/35936 A1 | 6/2000 |
| WO | WO 00/35939 A2 | 6/2000 |
| WO | 01/15729 A1 | 3/2001 |
| WO | WO 01/29217 A2 | 4/2001 |
| WO | WO 01/85941 A2 | 11/2001 |
| WO | WO 03/053340 A2 | 7/2003 |
| WO | 2005/049582 A1 | 6/2005 |
| WO | WO 2005/050202 A2 | 6/2005 |

(Continued)

OTHER PUBLICATIONS

Abreu JG, Ketpura NI, Reversade B, De Robertis EM. Connective-tissue growth factor (CTGF) modulates cell signalling by BMP and TGF-beta. Nat Cell Biol 2002;4(8):599-604.
Adler et al., "Glomerular mRNAs in Human Type 1 Diabetes: Biochemical Evidence for Microalbuminuria as a Manifestation of Diabetic Nephropathy" Kidney International (2001) 2330-2336.
Agrawal et al. (2000) "Antisense Therapeutics: Is It As Simple As Complementary Base Recognition?" Molecular Med. Today, 6:72-81.
Allawi et al., "Mapping of RNA accessible sites by extension of random oligonucleotide libraries with reverse transcriptase" RNA (2001) 7:314-327.

(Continued)

*Primary Examiner* — Sean McGarry
(74) *Attorney, Agent, or Firm* — Lando & Anastasi LLP

(57) ABSTRACT

This invention provides compounds which comprise modified oligonucleotides capable of inhibitory expression of connective tissue factor and composition containing same as well as methods of treating hyperprolific disorders and fibrotic diseases, and of reducing scarring resulting from wound healing using such compounds.

27 Claims, 12 Drawing Sheets

(56) References Cited

FOREIGN PATENT DOCUMENTS

| | | |
|---|---|---|
| WO | WO 2005/050203 A2 | 6/2005 |
| WO | WO 2005/077413 A1 | 8/2005 |
| WO | WO 2005/110479 A2 | 11/2005 |
| WO | WO 2005/117941 A2 | 12/2005 |
| WO | WO 2005/120231 A1 | 12/2005 |
| WO | WO 2006/069637 A1 | 6/2006 |
| WO | WO 2006/122046 A2 | 11/2006 |
| WO | WO 2007/040636 A1 | 4/2007 |
| WO | WO 2008/050329 A2 | 5/2008 |
| WO | WO 2009/044392 A2 | 4/2009 |
| WO | WO 2010/027830 A2 | 3/2010 |
| WO | WO 2010/027831 A1 | 3/2010 |
| WO | WO 2010/033246 A1 | 3/2010 |
| WO | WO 2010/036111 A1 | 4/2010 |
| WO | WO 2010/042201 A1 | 4/2010 |
| WO | WO 2010/042202 A1 | 4/2010 |
| WO | WO 2010/042281 A2 | 4/2010 |
| WO | WO 2010/107952 A2 | 9/2010 |
| WO | WO 2011/002525 A1 | 1/2011 |

OTHER PUBLICATIONS

Allen, J.T. et al. (1999) "Enhanced insulin-like growth factor binding protein-related protein 2 (Connective tissue growth factor) expression in patients with idiopathic pulmonary fibrosis and pulmonary sarcoidosis," Am. J. Respir. Cell Mol. Biol. 21(6):693-700.

Babic et al., "Fisp112/mouse connective tissue growth factol mediates endothelial cell adhesion and migration through integrin alphavbeta3, promotes endothelial cell survival and induces angiogenesis in vivo" Mol. Cell Biol. (1999) 19:2958-2966.

Blalock TD, Duncan MR, Varela JC, Goldstein MH, Tuli SS, Grotendorst GR, et al. Connective tissue growth factor expression and action in human corneal fibroblast cultures and rat corneas after photorefractive keratectomy. Invest Ophthalmol Vis Sci 2003;44(5):1879-87.

Boes et al., "Connective tissue growth factor (IGFBP-rP2) expression and regulation in cultured bovine endothelial cells" Endocrinology (1999) 140:1575-1580.

Bonniaud P, Margetts PJ, Kolb M, Haberberger T, Kelly M, Robertson J, et al. Adenoviral gene transfer of connective tissue growth factor in the lung induces transient fibrosis. Am J Respir Crit Care Med 2003;168(7):770-8.

Bradham, D.M. et al. (1991) "Connective tissue growth factor: a cysteine-rich mitogen secreted by human vascular endothelial cells is related to the SRC-induced immediate early gene product CEF-10," J. Cell Biol., 114:1285-1294.

Chirilla et al. (2002) "The Use of Synthetic Polymer for Delivery of Therapeutic Antisense Oligodeoxynucleotides" Biomaterials, 23:321-342.

Colwell AS, Phan TT, Kong W, Longaker MT, Lorenz PH. Hypertrophic scar fibroblasts have increased connective tissue growth factor expression after transforming growth factor-beta stimulation. Plast Reconstr Surg 2005;116(5):1387-90; discussion 91-2.

Colwell AS, Krummel TM, Longaker MT, Lorenz HP. Fetal and adult fibroblasts have similar TGF-beta-mediated, Smad-dependent signaling pathways. Plast Reconstr Surg. 2006;117(7):2277-83.

Crooke (2004) "Progress in Antisense Technology" Ann. Rev. Medicine, 55:61-95.

Dammeier J, Beer HD, Brauchle M, Werner S. Dexamethasone is a novel potent inducer of connective tissue growth factor expression. Implications for glucocorticoid therapy. J Biol Chem 1998;273(29):18185-90.

Duncan, M.R. et al. (1999) "Connective tissue growth factor mediates transforming growth factor β-induced collagen synthesis: down-regulation by cAMP," FASEB J. 1999 13:1774-1786.

Dunn et al., Accession No. AZ781130 on database rst.seq, Feb. 16, 2001.

Frazier K, Williams S, Kothapalli D, Klapper H, Grotendorst GR. Stimulation of fibroblast cell growth, matrix production, and granulation tissue formation by connective tissue growth factor. J Invest Dermatol 1996;107(3):404-11.

Grotendorst GR. Connective tissue growth factor: a mediator of TGF-beta action on fibroblasts. Cytokine Growth Factor Rev 1997;8(3):171-9.

Grotendorst GR, Rahmanie H, Duncan MR. Combinatorial signaling pathways determine fibroblast proliferation and myofibroblast differentiation. Faseb J 2004;18(3):469-79.

Hillier et al., Accession No. R06912 on database rst.seq, Apr. 5, 1995.

Hishikawa, K. et al. (1999) "Connective Tissue Growth Factor Induces Apoptosis in Human Breast Cancer Cell Line MCF-7," J. Biol. Chem., 274:37461-37466.

Hishikawa, K. et al. (1999) "Transforming growth factor-β1 induces apoptosis via connective tissue growth factor in human aortic smooth muscle cells," Eur. J. Pharmacol., 385:287-290.

Hishikawa, K. et al. (2001) "Static Pressure Regulates Connective Tissue Growth Factor Expression in Human Mesangial Cells," J. Biol. Chem., 276:16797-16803.

Ho et al., "Mapping of RNA accessible sites for antisense experiments with oligonucleotide libraries" Nature Biotech. (1998) 16:59-63.

Igarashi A, Okochi H, Bradham DM, Grotendorst GR. Regulation of connective tissue growth factor gene expression in human skin fibroblasts and during wound repair. Mol Biol Cell 1993;4(6):637-45.

Igarashi A, Nashiro K, Kikuchi K, Sato S, Ihn H, Fujimoto M, et al. Connective tissue growth factor gene expression in tissue sections from localized scleroderma, keloid, and other fibrotic skin disorders. The Journal of investigative dermatology 1996;106(4):729-33.

Ito, Y. et al. (2001) "Kinetics of Connective Tissue Growth Factor Expression during Experimental Proliferative Glomerulonephritis," J. Am. Soc. Nephrol., 12:472-484.

Jang et al. (2004) "Gene Delivery From Polymer Scaffolds For Tissue Engineering," Expert Rev. Medical Devices, 1:127-138.

Jedsadayanmata et al., "Activation-dependent adhesion of human platelets to Cyr61 and Fisp12/mouse connective tissue growth factor is mediated through integrin alpha(IIb)beta(3)" J. Biol. Chem. (1999) 274:24321-24327.

Kasaragod, A.B. et al. (2001) "Connective Tissue Growth Factor Expression in Pediatric Myofibroblastic Tumors," Pediatr. Dev. Pathol., 4:37-45.

Kim et al., "Identification of a family of low-affinity insulin-like growth factor binding proteins (IGFBPs): characterization of connective tissue growth factor as a member of the IGFBP superfamily" PNAS (1997) 94:12981-12986.

Kondo, S. at al. (2000) "Characterization of a Mouse ctgf 3'-UTR Segment That Mediates Repressive Regulation of Gene Expression," Biochem. Biophys. Res. Commun., 278:119-124.

Kothapalli, D. et al. (1997) "Transforming growth factor beta induces anchorage-independent growth of NRK fibroblasts via a connective tissue growth factor-dependent signaling pathway," Cell Growth Diff., 8:61-68.

Kryger ZB, Sisco M, Roy NK, Lu L, Rosenberg D, Mustoe TA. Temporal expression of the transfo ming growth factor-Beta pathway in the rabbit ear model of wound healing and scarring. J Am Coll Surg 2007;205(1):78-88.

Kubota, S. et al. (1999) "Involvement of cis-acting repressive element(s) in the 3'-untranslated region of human connective tissue growth factor gene," FEBS Lett., 450:84-88.

Lasky, J.A. et al. (1998) "Connective tissue growth factor mRNA expression is upregulated in bleomycin-induced lung fibrosis," Am. J. Physiol., 275:L365-L371.

Lau, L.F. et al. (1999) "The CCN Family of Angiogenic Regulators: The Integrin Connection," Exp. Cell Res., 248:44-57.

Leask A, and Abraham DJ. TGF-beta signaling and the fibrotic response. Faseb J 2004;18(7):816-27.

Lin CG, Chen CC, Leu SJ, Grzeszkiewicz TM, Lau LF. Integrin-dependent functions of the angiogenic inducer NOV (CCN3): implication in wound healing. J Biol Chem 2005;280 (9): 8229-37.

Lopez-Bermejo et al., "Characterization of insulin-like growth factor-binding protein-related proteins (IGFBP-rPs) 1, 2, and 3 in human prostate epithelial cells: potential roles for IGFBP-rP1 and 2 in senescence of the prostatic epithelium" Endocrinology (2000) 141:4072-4080.

(56) References Cited

OTHER PUBLICATIONS

Lu et al. (2005) "The Temporal Effects of Anti-TGF-β1, 2, and 3 Monoclonal Antibody on Wound Healing and Hypertrophic Scar Formation," J. Am. Coll. Surg., 201:391-397.
Martinerie, C. et al. (1992) "Physical mapping of human loci homologous to the chicken nov proto-oncogene," Oncogene, 7:2529-2534 (Abstract only).
Matveeva et al., "A rapid in vitro method for obtaining RNA accessibility patterns for complementary DNA probes: correlation with an intracellular pattern and known RNA structures" Nucleic Acids Res. (1997) 25:5010-5016.
Milner et al., "Selecting effective antisense reagents on combinatorial oligonucleotide arrays" Nature Biotech (1997) 15:537-541.
Moussad, E.A. et al. (2000) "Connective Tissue Growth Factor: What's in a Name?" Mol. Genet. Metab., 71:276-292.
Mustoe TA, Pierce GF, Morishima C, Deuel TF. Growth factor-induced acceleration of tissue repair through direct and inductive activities in a rabbit dermal ulcer model. J Clin Invest 1991;87(2):694-703.
Mustoe TA. Scars and keloids. BMJ Clinical research ed 2004; 328(7452):1329-30.
Nakanishi et al., "Overexpression of connective tissue growth factor/hypertrophic chondrocyte-specific gene products 24 decreases bone density in adult mice and induces dwarfism" Biochem. Biophys. Res. Commun. (2001) 281:678-681.
Opalinska et al. (2002) "Nucleic-Acid Therapeutics: Basic Principles and Recent Applications" Nature Review, 1:503-514.
Patzel et al., "Theoretical design of antisense RNA structures substantially improves annealing kinetics and efficacy in human cells" Nature Biotech (1998) 16:64-68.
Patzel et al., "A theoretical approach to select effective antisense oligodeoxyribonucleotides at high statistical probability" Nucleic Acids Res. (1999) 27:4328-4334.
Pereira et al., "Transcriptional regulation of connective tissue growth factor by cortisol in osteoblasts" Am. J. Physiol. Endocrinol. Metab. (2000) 279:E570-E576.
Perrachi (2004) "Prospects for Antiviral Ribozymes and Deoxyribozymes" Rev. Med. Virol., 14:47-64.
Reid RR, Mogford JE, Butt R, deGiorgio-Miller A, Mustoe TA. Inhibition of procollagen C-proteinase reduces scar hypertrophy in a rabbit model of cutaneous scarring. Wound Repair Regen 2006; 14 (2) : 138-41.
Riser BL, Denichilo M, Cortes P, Baker C, Grondin JM, Yee J, et al. Regulation of connective tissue growth factor activity in cultured rat mesangial cells and its expression in experimental diabetic glomerulosclerosis. J Am Soc Nephrol 2000;11(1):25-38.
Riser et al., "Urinary CCN (CTGF) as a Possible Predictor of Diabetic Nephropathy: Preliminary Report" Kidney International (2003) 64:451-458.
Santos et al. (2005) "Intraocular Delivery of Oligonucleotides," Curr. Pharm. Biotech., 6:7-15.
Shi-wen X, Pennington D, Holmes A, Leask A, Bradham D, Beauchamp JR, et al. Autocrine overexpression of CTGF maintains fibrosis: RDA analysis of fibrosis genes in systemic sclerosis. Exp Cell Res 2000;259(1):213-24.
Shimo, T. et al. (1998) "Inhibition of Endogenous Expression of Connective Tissue Growth Factor by Its Antisense Oligonucleotide and Antisense RNA Suppresses Proliferation, and Migration of Vascular Endothelial Cells," J. Biochem., 124:130-140.
Shull MM, Ormsby I, Kier AB, Pawlowski S, Diebold RJ, Yin M, al. Targeted disruption of the mouse transforming growth factor-beta 1 gene results in multifocal inflammatory disease. Nature 1992;359(6397) :693-9.
Sisco M, Kryger ZB, Jia SC, Schultz GS, Dean NM, Mustoe TA. Antisense oligonucleotides against transforming growth factor-beta delay wound healing in a rabbit ear model. J Am Coll Surg 2005;201:S60.

Sisco at al. (2008) "Antisense Inhibition of Connective Tissue Growth Factor (CTGF/CCN2) mRNA Limits Hypertrophic Scarring Without Affecting Wound Healing In Vivo," Wound Rep. Reg. 16:661-673.
Tsubaki, J. et al. (2001) "Effects of sodium butyrate on expression of members of the IGF-binding protein superfamily in human mammary epithelial cells," J. Endocrinol., 169:97-110.
Twigg et al., "Advanced glycosylation end products up-regulate connective tissue growth factor (insulin-like growth factor-binding protein-related protein 2) in human fibroblasts: a potential mechanism for expansion of extracellular matrix in diabetes mellitus" Endocrinology (2001) 142:1760-1769.
Vorwerk, P. et al, (2000) "CTGF (IGFBP-rP2) is specifically expressed in malignant lymphoblasts of patients with acute lymphoblastic leukaemia (ALL)," Brit. J. Cancer, 83:756-760.
Wahab et al., "Role of connective tissue growth factor in the pathogenesis of diabetic nephropathy" Biochem. J. (2001) 359:77-87.
Wahab et al., "Connective tissue growth factor and regulation of the mesangial cell cycle: role in cellular hypertrophy" J. Am. Soc. Nephrol. (2002) 13:2437-2445.
Walton et al., "Prediction of antisense oligonucleotide binding affinity to a structured RNA target" Biotechnology and Bioengineering (1999) 65:1-9.
Wang JF, Olson ME, Ma L, Brigstock DR, Hart DA. Connective tissue growth factor siRNA modulates mRNA levels for a subset of molecules in normal and TGF-beta 1-stimulated porcine skin fibroblasts. Wound Repair Regen 2004;12(2):205-16.
Yang, D,H. et al. (1998) "Identification of Glycosylated 38-kDa Connective Tissue Growth Factor (IGFBP-Related Protein 2) and Proteolytic Fragments in Human Biological Fluids, and Up-Regulation of IGFBP-rP2 Expression by TGF-β in Hs578T Human Breast Cancer Cells," J. Chin. Endocrinol. Metab., 83:2593-2596.
Yokoi et al,, "Role of connective tissue growth factor in profibrotic action of transforming growth factor-Beta: a potential target for preventing renal fibrosis" Am. J. Kidney Disease (2001) 38(4 Suppl. 1):S134-S138.
Yokoi et al., "Role of connective tissue growth factor in fibronectin expression and tubulointerstitial fibrosis" Am. J. Physiol. Renal Physiol. (2002) 282:F933-F942.
Zhang H, Cook J, Nickel J, Yu R, Stecker K, Myers K, et al. Reduction of liver Fas expression by an antisense oligonucleotide protects mice from fulminant hepatitis. Nat Biotechnol 2000;18(8):862-7.
Office Action issued May 19, 2004 in connection with U.S. Appl. No. 10/006,191.
Response filed Sep. 20, 2004 in connection with U.S. Appl. No. 10/006,191.
Office Action issued Dec. 2, 2004 in connection with U.S. Appl. No. 10/006,191.
Response filed Feb. 2, 2005 in connection with U.S. Appl. No. 10/006,191.
Advisory Action issued Feb. 17, 2005 in connection with U.S. Appl. No. 10/006,191.
Office Action issued Apr. 17, 2007 in connection with U.S. Appl. No. 10/946,914.
Response filed Aug. 15, 2007 in connection with U.S. Appl. No. 10/946,914.
Office Action issued Oct. 31, 2007 in connection with U.S. Appl. No. 10/946,914.
Office Action issued May 26, 2009 in connection with U.S. Appl. No. 11/985,843.
Examiner Interview Summary issued Sep. 11, 2009 in connection with U.S. Appl. No. 11/985,843.
Response filed Nov. 27, 2009 in connection with U.S. Appl. No. 11/985,843.
Office Action issued Mar. 12, 2010 in connection with U.S. Appl. No. 11/985,843.
Preliminary Amendment filed Dec. 9, 2008 in connection with U.S. Appl. No. 12/011,761.
Office Action issued Jun. 17, 2011 in connection with U.S. Appl. No. 13/007,900.
Office Action issued Feb. 29, 2012 in connection with U.S. Appl. No. 13/329,095.

(56) References Cited

OTHER PUBLICATIONS

Office Action issued Mar. 31, 2011 in connection with U.S. Appl. No. 12/547,481.
Amendment in Response to Mar. 31, 2011 Office Action file Sep. 30, 2011 in connection with U.S. Appl. No. 12/547,481.
Office Action issued Nov. 29, 2011 in connection with U.S. Appl. No. 12/547,481.
Combined Search and Examination Report issued Jun. 22, 2010 in connection with British Patent Application No. GB1002626.8.
Examination Report issued Jun. 8, 2011 in connection with New Zealand Patent Application No. 591416.
Supplemental European Search Report for EP 09 81 9622 dated Dec. 13, 2012.

| Oligonucleotide # | Sequence |
|---|---|
| 412404 | CGTGGCAAGAGCCCTAAGTT (INTRON) |
| 412283 | GGGCATGCAGCCCACCGCCC (EXON 3) |
| 412285 | AGGGCAGGCCCAACCACGGT (EXON 3) |
| 412294 | GTTTGACATGGCACAATGTT (EXON 5) |
| 412295 | TATTTGTTTGACATGGCACA (EXON 5) |
| 412300 | TAATATACATTCTGGTGCTG (EXON 5) |
| 412307 | TACACTTCAAATAGCAGGCA (EXON 5) |
| 412311 | TCTTGATGGCTGGAGAATGC (EXON 5) |
| 412333 | CAGCCTGCCAAGGACACTGA (EXON 5) |
| 124238 | AAACATGTAACTTTTGGTCA (Old leads) |
| 124212 | CCACAAGCTGTCCAGTCTAA (Old leads) |

SEQUENCE LISTING

```
<160> NUMBER OF SEQ ID NOS: 167

<210> SEQ ID NO 1
<211> LENGTH: 20
<212> TYPE: DNA
<213> ORGANISM: Artificial Sequence
<220> FEATURE:
<223> OTHER INFORMATION: Positive control oligonucleotide directed to
      human H-ras

<400> SEQUENCE: 1
tccgtcatcg ctcctcaggg                                                    20

<210> SEQ ID NO 2
<211> LENGTH: 2075
<212> TYPE: DNA
<213> ORGANISM: Homo sapiens
<220> FEATURE:
<221> NAME/KEY: exon
<222> LOCATION: (130)..(1180)

<400> SEQUENCE: 2
cccggccgac agccccgaga cgacagcccg gcgcgtcccg gtccccacct ccgaccaccg        60
ccagcgctcc aggccccgcg ctccccgctc gccgccaccg cgccctccgc tccgcccgca       120 gtgccaacc atg acc gcc gcc agt atg ggc ccc gtc cgc gtc gcc ttc gtg      171
          Met Thr Ala Ala Ser Met Gly Pro Val Arg Val Ala Phe Val
            1               5                  10 gtc ctc ctc gcc ctc tgc agc cgg ccg gcc gtc ggc cag aac tgc agc        219
Val Leu Leu Ala Leu Cys Ser Arg Pro Ala Val Gly Gln Asn Cys Ser
15                  20                  25                  30
```

| | | |
|---|---|---|
| ggg ccg tgc cgg tgc ccg gac gag ccg gcg ccg cgc tgc ccg gcg ggc | 267 | |
| Gly Pro Cys Arg Cys Pro Asp Glu Pro Ala Pro Arg Cys Pro Ala Gly | | |
|             35            40            45 | | |

```
ggg ccg tgc cgg tgc ccg gac gag ccg gcg ccg cgc tgc ccg gcg ggc       267
Gly Pro Cys Arg Cys Pro Asp Glu Pro Ala Pro Arg Cys Pro Ala Gly
             35                  40                  45 gtg agc ctc gtg ctg gac ggc tgc ggc tgc tgc cgt gtc tgc gcc aag       315
Val Ser Leu Val Leu Asp Gly Cys Gly Cys Cys Arg Val Cys Ala Lys
             50                  55                  60 cag ctg ggc gag ctg tgc acc gag cgc gac ccc tgc gac ccg cac aag       363
Gln Leu Gly Glu Leu Cys Thr Glu Arg Asp Pro Cys Asp Pro His Lys
             65                  70                  75 ggc ctc ttc tgt gac ttc ggc tcc ccg gcc aac cgc aag atc ggc gtg       411
Gly Leu Phe Cys Asp Phe Gly Ser Pro Ala Asn Arg Lys Ile Gly Val
     80                  85                  90 tgc acc gcc aaa gat ggt gct ccc tgc atc ttc ggt ggt acg gtg tac       459
Cys Thr Ala Lys Asp Gly Ala Pro Cys Ile Phe Gly Gly Thr Val Tyr
 95             100                 105                 110 cgc agc gga gag tcc ttc cag agc agc tgc aag tac cag tgc acg tgc       507
Arg Ser Gly Glu Ser Phe Gln Ser Ser Cys Lys Tyr Gln Cys Thr Cys
                115                 120                 125 ctg gac ggg gcg gtg ggc tgc atg ccc ctg tgc agc atg gac gtt cgt       555
Leu Asp Gly Ala Val Gly Cys Met Pro Leu Cys Ser Met Asp Val Arg
            130                 135                 140 ctg ccc agc cct gac tgc ccc ttc ccg agg agg gtc aag ctg ccc ggg       603
Leu Pro Ser Pro Asp Cys Pro Phe Pro Arg Arg Val Lys Leu Pro Gly
            145                 150                 155 aaa tgc tgc gag gag tgg gtg tgt gac gag ccc aag gac caa acc gtg       651
Lys Cys Cys Glu Glu Trp Val Cys Asp Glu Pro Lys Asp Gln Thr Val
160                 165                 170 gtt ggg cct gcc ctc gcg gct tac cga ctg gaa gac acg ttt ggc cca       699
Val Gly Pro Ala Leu Ala Ala Tyr Arg Leu Glu Asp Thr Phe Gly Pro
175                 180                 185                 190 gac cca act atg att aga gcc aac tgc ctg gtc cag acc aca gag tgg       747
Asp Pro Thr Met Ile Arg Ala Asn Cys Leu Val Gln Thr Thr Glu Trp
                195                 200                 205 agc gcc tgt tcc aag acc tgt ggg atg ggc atc tcc acc cgg gtt acc       795
Ser Ala Cys Ser Lys Thr Cys Gly Met Gly Ile Ser Thr Arg Val Thr
            210                 215                 220 aat gac aac gcc tcc tgc agg cta gag aag cag agc cgc ctg tgc atg       843
Asn Asp Asn Ala Ser Cys Arg Leu Glu Lys Gln Ser Arg Leu Cys Met
            225                 230                 235 gtc agg cct tgc gaa gct gac ctg gaa gag aac att aag aag ggc aaa       891
Val Arg Pro Cys Glu Ala Asp Leu Glu Glu Asn Ile Lys Lys Gly Lys
240                 245                 250 aag tgc atc cgt act ccc aaa atc tcc aag cct atc aag ttt gag ctt       939
Lys Cys Ile Arg Thr Pro Lys Ile Ser Lys Pro Ile Lys Phe Glu Leu
255                 260                 265                 270 tct ggc tgc acc agc atg aag aca tac cga gct aaa ttc tgt gga gta       987
Ser Gly Cys Thr Ser Met Lys Thr Tyr Arg Ala Lys Phe Cys Gly Val
                275                 280                 285 tgt acc gac ggc cga tgc tgc acc ccc cac aga acc acc acc ctg ccg      1035
Cys Thr Asp Gly Arg Cys Cys Thr Pro His Arg Thr Thr Thr Leu Pro
            290                 295                 300 gtg gag ttc aag tgc cct gac ggc gag gtc atg aag aag aac atg atg      1083
Val Glu Phe Lys Cys Pro Asp Gly Glu Val Met Lys Lys Asn Met Met
            305                 310                 315 ttc atc aag acc tgt gcc tgc cat tac aac tgt ccc gga gac aat gac      1131
Phe Ile Lys Thr Cys Ala Cys His Tyr Asn Cys Pro Gly Asp Asn Asp
            320                 325                 330 atc ttt gaa tcg ctg tac tac agg aag atg tac gga gac atg gca tga a   1180
Ile Phe Glu Ser Leu Tyr Tyr Arg Lys Met Tyr Gly Asp Met Ala
335                 340                 345
```

-continued

```
gccagagagt gagagacatt aactcattag actggaactt gaactgattc acatctcatt    1240
tttccgtaaa aatgatttca gtagcacaag ttatttaaat ctgtttttct aactggggga    1300
aaagattccc acccaattca aaacattgtg ccatgtcaaa caaatagtct atcttcccca    1360
gacactggtt tgaagaatgt taagacttga cagtggaact acattagtac acagcaccag    1420
aatgtatatt aaggtgtggc tttaggagca gtgggagggt accggcccgg ttagtatcat    1480
cagatcgact cttatacgag taatatgcct gctatttgaa gtgtaattga gaaggaaaat    1540
tttagcgtgc tcactgacct gcctgtagcc ccagtgacag ctaggatgtg cattctccag    1600
ccatcaagag actgagtcaa gttgttcctt aagtcagaac agcagactca gctctgacat    1660
tctgattcga atgacactgt tcaggaatcg gaatcctgtc gattagactg gacagcttgt    1720
ggcaagtgaa tttgcctgta acaagccaga ttttttaaaa tttatattgt aaatattgtg    1780
tgtgtgtgtg tgtgtgtata tatatatata tatgtacagt tatctaagtt aatttaaagt    1840
tgtttgtgcc tttttatttt tgtttttaat gctttgatat ttcaatgtta gcctcaattt    1900
ctgaacacca taggtagaat gtaaagcttg tctgatcgtt caaagcatga aatggatact    1960
tatatggaaa ttctgctcag atagaatgac agtccgtcaa aacagattgt ttgcaaaggg    2020
gaggcatcag tgtcttggca ggctgatttc taggtaggaa atgtggtagc tcacg         2075
```

<210> SEQ ID NO 3
<211> LENGTH: 22
<212> TYPE: DNA
<213> ORGANISM: Artificial Sequence
<220> FEATURE:
<223> OTHER INFORMATION: Forward PCR primer directed to human connective
      tissue growth factor (CTGF)

<400> SEQUENCE: 3
acaagggcct cttctgtgac tt                                              22

<210> SEQ ID NO 4
<211> LENGTH: 22
<212> TYPE: DNA
<213> ORGANISM: Artificial Sequence
<220> FEATURE:
<223> OTHER INFORMATION: Reverse PCR primer directed to human connective
      tissue growth factor (CTGF)

<400> SEQUENCE: 4
ggtacaccgt accaccgaag at                                              22

<210> SEQ ID NO 5
<211> LENGTH: 23
<212> TYPE: DNA
<213> ORGANISM: Artificial Sequence
<220> FEATURE:
<223> OTHER INFORMATION: PCR probe directed to human connective tissue
      growth factor (CTGF)

<400> SEQUENCE: 5
tgtgcaccgc caaagatggt gct                                             23

<210> SEQ ID NO 6
<211> LENGTH: 19
<212> TYPE: DNA
<213> ORGANISM: Artificial Sequence
<220> FEATURE:
<223> OTHER INFORMATION: Forward PCR primer directed to human GAPDH

<400> SEQUENCE: 6

```
gaaggtgaag gtcggagtc                                                    19

<210> SEQ ID NO 7
<211> LENGTH: 20
<212> TYPE: DNA
<213> ORGANISM: Artificial Sequence
<220> FEATURE:
<223> OTHER INFORMATION: Reverse PCR primer directed to human GAPDH

<400> SEQUENCE: 7
gaagatggtg atgggatttc                                                   20

<210> SEQ ID NO 8
<211> LENGTH: 20
<212> TYPE: DNA
<213> ORGANISM: Artificial Sequence
<220> FEATURE:
<223> OTHER INFORMATION: PCR probe directed to human GAPDH

<400> SEQUENCE: 8
caagcttccc gttctcagcc                                                   20

<210> SEQ ID NO 9
<211> LENGTH: 2358
<212> TYPE: DNA
<213> ORGANISM: Homo sapiens
<220> FEATURE:
<221> NAME/KEY: exon
<222> LOCATION: (207)..(1256)

<400> SEQUENCE: 9
aaactcacac aacaactctt ccccgctgag aggagacagc cagtgcgact ccaccctcca       60
gctcgacggc agccgccccg ccgacagcc ccgagacgac agcccggcgc gtcccggtcc       120
ccacctccga ccaccgccag cgctccaggc cccgccgctc cccgctcgcc gccaccgcgc      180
cctccgctcc gcccgcagtg ccaacc atg acc gcc gcc agt atg ggc ccc gtc       233
                              Met Thr Ala Ala Ser Met Gly Pro Val
                                1               5 cgc gtc gcc ttc gtg gtc ctc ctc gcc ctc tgc agc cgg ccg gcc gtc        281
Arg Val Ala Phe Val Val Leu Leu Ala Leu Cys Ser Arg Pro Ala Val
 10                  15                  20                  25 ggc cag aac tgc agc ggg ccg tgc cgg tgc ccg gac gag ccg gcg ccg        329
Gly Gln Asn Cys Ser Gly Pro Cys Arg Cys Pro Asp Glu Pro Ala Pro
                 30                  35                  40 cgc tgc ccg gcg ggc gtg agc ctc gtg ctg gac ggc tgc ggc tgc tgc        377
Arg Cys Pro Ala Gly Val Ser Leu Val Leu Asp Gly Cys Gly Cys Cys
             45                  50                  55 cgc gtc tgc gcc aag cag ctg ggc gag ctg tgc acc gag cgc gac ccc        425
Arg Val Cys Ala Lys Gln Leu Gly Glu Leu Cys Thr Glu Arg Asp Pro
         60                  65                  70 tgc gac ccg cac aag ggc ctc ttc tgt gac ttc ggc tcc ccg gcc aac        473
Cys Asp Pro His Lys Gly Leu Phe Cys Asp Phe Gly Ser Pro Ala Asn
     75                  80                  85 cgc aag atc ggc gtg tgc acc gcc aaa gat ggt gct ccc tgc atc ttc        521
Arg Lys Ile Gly Val Cys Thr Ala Lys Asp Gly Ala Pro Cys Ile Phe
 90                  95                 100                 105 ggt ggt acg gtg tac cgc agc gga gag tcc ttc cag agc agc tgc aag        569
Gly Gly Thr Val Tyr Arg Ser Gly Glu Ser Phe Gln Ser Ser Cys Lys
                110                 115                 120 tac cag tgc acg tgc ctg gac ggg gcg gtg ggc tgc atg ccc ctg tgc        617
Tyr Gln Cys Thr Cys Leu Asp Gly Ala Val Gly Cys Met Pro Leu Cys
            125                 130                 135
```

```
agc atg gac gtt cgt ctg ccc agc cct gac tgc ccc ttc ccg agg agg      665
Ser Met Asp Val Arg Leu Pro Ser Pro Asp Cys Pro Phe Pro Arg Arg
        140                 145                 150 gtc aag ctg ccc ggg aaa tgc tgc gag gag tgg gtg tgt gac gag ccc      713
Val Lys Leu Pro Gly Lys Cys Cys Glu Glu Trp Val Cys Asp Glu Pro
155                 160                 165 aag gac caa acc gtg gtt ggg cct gcc ctc gcg gct tac cga ctg gaa      761
Lys Asp Gln Thr Val Val Gly Pro Ala Leu Ala Ala Tyr Arg Leu Glu
170                 175                 180                 185 gac acg ttt ggc cca gac cca act atg att aga gcc aac tgc ctg gtc      809
Asp Thr Phe Gly Pro Asp Pro Thr Met Ile Arg Ala Asn Cys Leu Val
                190                 195                 200 cag acc aca gag tgg agc gcc tgt tcc aag acc tgt ggg atg ggc atc      857
Gln Thr Thr Glu Trp Ser Ala Cys Ser Lys Thr Cys Gly Met Gly Ile
                205                 210                 215 tcc acc cgg gtt acc aat gac aac gcc tcc tgc agg cta gag aag cag      905
Ser Thr Arg Val Thr Asn Asp Asn Ala Ser Cys Arg Leu Glu Lys Gln
            220                 225                 230 agc cgc ctg tgc atg gtc agg cct tgc gaa gct gac ctg gaa gag aac      953
Ser Arg Leu Cys Met Val Arg Pro Cys Glu Ala Asp Leu Glu Glu Asn
235                 240                 245 att aag aag ggc aaa aag tgc atc cgt act ccc aaa atc tcc aag cct     1001
Ile Lys Lys Gly Lys Lys Cys Ile Arg Thr Pro Lys Ile Ser Lys Pro
250                 255                 260                 265 atc aag ttt gag ctt tct ggc tgc acc agc atg aag aca tac cga gct     1049
Ile Lys Phe Glu Leu Ser Gly Cys Thr Ser Met Lys Thr Tyr Arg Ala
                270                 275                 280 aaa ttc tgt gga gta tgt acc gac ggc cga tgc tgc acc ccc cac aga     1097
Lys Phe Cys Gly Val Cys Thr Asp Gly Arg Cys Cys Thr Pro His Arg
                285                 290                 295 acc acc acc ctg ccg gtg gag ttc aag tgc cct gac ggc gag gtc atg     1145
Thr Thr Thr Leu Pro Val Glu Phe Lys Cys Pro Asp Gly Glu Val Met
            300                 305                 310 aag aag aac atg atg ttc atc aag acc tgt gcc tgc cat tac aac tgt     1193
Lys Lys Asn Met Met Phe Ile Lys Thr Cys Ala Cys His Tyr Asn Cys
315                 320                 325 ccc gga gac aat gac atc ttt gaa tcg ctg tac tac agg aag atg tac     1241
Pro Gly Asp Asn Asp Ile Phe Glu Ser Leu Tyr Tyr Arg Lys Met Tyr
330                 335                 340                 345 gga gac atg gca tga agccagagag tgagagacat taactcatta gactggaact     1296
Gly Asp Met Ala tgaactgatt cacatctcat ttttccgtaa aaatgatttc agtagcacaa gttatttaaa   1356 tctgttttc taactggggg aaaagattcc cacccaattc aaaacattgt gccatgtcaa    1416
acaaatagtc tatcaacccc agacactggt ttgaagaatg ttaagacttg acagtggaac   1476
tacattagta cacagcacca gaatgtatat taaggtgtgg ctttaggagc agtgggaggg   1536
taccagcaga aaggttagta tcatcagata gcatcttata cgagtaatat gcctgctatt   1596
tgaagtgtaa ttgagaagga aaattttagc gtgctcactg acctgcctgt agccccagtg   1656
acagctagga tgtgcattct ccagccatca agagactgag tcaagttgtt ccttaagtca   1716
gaacagcaga ctcagctctg acattctgat tcgaatgaca ctgttcagga atcggaatcc   1776
tgtcgattag actggacagc ttgtggcaag tgaatttgcc tgtaacaagc cagatttttt   1836
aaaatttata ttgtaaatat tgtgtgtgtg tgtgtgtgtg tatatatata tatatgtaca   1896
gttatctaag ttaatttaaa gttgtttgtg ccttttatt tttgttttta atgctttgat    1956
atttcaatgt tagcctcaat ttctgaacac cataggtaga atgtaaagct tgtctgatcg   2016
```

```
ttcaaagcat gaaatggata cttatatgga aattctgctc agatagaatg acagtccgtc    2076
aaaacagatt gtttgcaaag gggaggcatc agtgtccttg gcaggctgat ttctaggtag    2136
gaaatgtggt agcctcactt ttaatgaaca aatggccttt attaaaaact gagtgactct    2196
atatagctga tcagtttttt cacctggaag catttgtttc tactttgata tgactgtttt    2256
tcggacagtt tatttgttga gagtgtgacc aaaagttaca tgtttgcacc tttctagttg    2316
aaaataaagt gtatatttt tctataaaaa aaaaaaaaa aa                         2358

<210> SEQ ID NO 10
<211> LENGTH: 6001
<212> TYPE: DNA
<213> ORGANISM: Homo sapiens

<400> SEQUENCE: 10
tatattattc actgtcaatc ttagtttata tccagataca acagggtaca ctgctcttgt      60
aatggaatca gacttcttat tttaacaaga caaaccaaat ccaatccaca tttgaagatt     120
ataggtttta atataagaaa atgcactcat ttctcaaaga ccctagtgaa gctgtgttta     180
aatgctccta ggtgaacccc ctttgcatcc cagtgttccc accctgacac ccagagcccc     240
tacctaccca acacagaatc atttgctctg atagaacaat ggatcccttt ttctggaaac     300
attgatggcc actcctccct tgtccttgcc tatataaaac tcctacatat attaagagaa     360
aactaagcaa gagttttgga aatctgcccc aggagactgc atcctgagtc acacgcgtct     420
ttgttctctt tcttgtccca aaaccgttac ctcaagtgac aaatgatcaa atctcaaata     480
tagaattcag ggttttacag gtaggcatct tgaggatttc aaatggttaa aagcaactca     540
ctccttttct actctttgga gagtttcaag agcctatagc ctctaaaacg caaatcattg     600
ctaagggttg gggggggagaa accttttcga attttttagg aattcctgct gtttgcctct     660
tcagctacct acttcctaaa aaggatgtat gtcagtggac agaacagggc aaacttattc     720 gaaaagaaa taagaaataa ttgccagtgt gtttataaat gatatgaatc aggagtggtg     780
cgaagaggat agggaaaaaa aaattctatt tggtgctgga aatactgcgc ttttttttt     840 cctttttttt tttttctgtg agctggagtg tgccagcttt ttcagacgga ggaatgctga     900
gtgtcaaggg gtcaggatca atccggtgtg agttgatgag gcaggaaggt ggggaggaat     960
gcgaggaatg tccctgtttg tgtaggactc cattcagctc attggcgagc gcggccgcc    1020 cggagcgtat aaaagcctcg ggccgcccgc cccaaactca cacaacaact cttccccgct    1080
gagaggagac agccagtgcg actccaccct ccagctcgac ggcagccgcc ccggccgaca    1140
gccccgagac gacagcccgg cgcgtcccgg tccccacctc cgaccaccgc cagcgctcca    1200
ggccccgccg ctccccgctc gccgccaccg cgccctccgc tccgcccgca gtgccaacca    1260
tgaccgccgc cagtatgggc cccgtccgcg tcgccttcgt ggtcctcctc gccctctgca    1320
gccgggtaag cgccgggagc cccgctgcg gccggcggct gccagggagg gactcgggc    1380 cggccgggga gggcgtgcgc gccgaccgag cgccgctgac cgccctgtcc tccctgcagc    1440
cggccgtcgg ccagaactgc agcgggccgt gcggtgccc ggacgagccg gcgccgcgct    1500
gccccggcgg cgtgagcctc gtgctggacg gctgcgctg ctgccgcgtc tgcgccaagc    1560
agctgggcga gctgtgcacc gagcgcgacc catgcgaccc gcacaagggc ctattctgtc    1620
acttcggctc cccggccaac cgcaagatcg gcgtgtgcac cggtaagacc gcagccccc    1680 accgctaggt gtccggccgc ctcctccctc acgcccaccc gcccgctgga aaagaaacc    1740
```

```
gctcggactg agtttctttc tccagctgct gccagcccgc cccctgcagc ccagatccca    1800
actcgcatcc ctgacgctct ggatgtgaga gtgccccaat gcctgacctc tgcatccccc    1860
acccctctct tcccttcctc ttctccagcc aaagatggtg ctccctgcat cttcggtggt    1920
acggtgtacc gcagcggaga gtccttccag agcagctgca agtaccagtg cacgtgcctg    1980
gacggggcgg tgggctgcat gcccctgtgc agcatggacg ttcgtctgcc cagccctgac    2040
tgccccttcc cgaggagggt caagctgccc gggaaatgct gcgaggagtg ggtgtgtgac    2100
gagcccaagg accaaaccgt ggttgggcct gccctcgcgg gtgagtcgag tcttcctcta    2160
agtcagggtc gtgattctct cccagggagg gagtcctaac tgtgccgacc gaacggggga    2220 aatacccttat ccaggcgttt tacatggtgt tgtgtgctc tgctctcgca gcttaccgac    2280
```

```
tttgtttcta ctttgatatg actgtttttc ggacagttta tttgttgaga gtgtgaccaa    4200
aagttacatg tttgcacctt tctagttgaa aataaagtgt atatttttc tataaagggc    4260 ttggttattc atttatcctt ctaaacattt ctgagttttc ttgagcataa ataggaagtt    4320
cttattaatc ataagataat tcaccaataa ttttctaaat atctttaatt attctataca    4380
ttaataaatt gattattcca tagaattttt atgtaaacat acttcacact gaatcaagta    4440
tcacagactt gcaggcatac acaccacatt gactatacag ccattttttt tgttatcttc    4500
acagaacttt atagacactt taaattcaat tctctctaga ttacttcagt ctccattaac    4560
cctgttgtat tacacttggt cctttttggca tttgtacctc tctggccgtt ataggttagt    4620
ttccaaccct tcacatcaca aactagtcta tgtgccttgc acgtggaaaa tgtttacatt    4680
ttttaaaaat tttatgctct aggtctgttt ctgaacttca ttaccttact gttaaatctg    4740
aaaattatga aatgaaatcc tcatttaaat ggagctattt cataagtctt gttttgtata    4800
attccgtttt tggttgccat gataaccaat gacaaacaga tggcataaat agaaaaggga    4860
ggatgagcaa atcttccatt cattaacatt aatagaaatt tgttttgaaa gtaattcctc    4920
catttgccca agtctttagc tttatcagac ttcagattta atgcatccta ccttaccaag    4980
tggtttatac atgagaaaat ggaattgttc aagaagcctc atgtggaaac aatattgtac    5040
ctacccaggt aggttttttac taagagtga accaaagtga atggtaaaca aaagcaatac    5100
accaaaggca actagaatct tctccacatg aggatagctg aggattctag gggaaaaaaa    5160
aattgcagac agactaactt ttcccaaggt aattagcaac gttgtagtgc caatgtcatt    5220
tggacagaca aaaatacacc tgaaaataaa gactagctct acaaacaact gtccacacca    5280
caaaccaaag ggaaaacttc ccgtgttcag aatgtgaaaa tttatggtca aaactctggg    5340
ctttaaggat acacccacat ctgtatatag cagtgctgcc aggagcagca ccccacctcc    5400
ccaaataaat gcgcatgtac acatacacat aggcacacac acagagtaca ctgttagttc    5460
acacttcctt tctgtcaatt aattcctaac tgcaaagatg aagggccatg catgataaac    5520
gagactgact actgaattag agcattctgg aaatatagaa gcagcaggaa aagcatagat    5580
ttcacatttt ccaaatacccc acattaaaga aaaaaaaag agtcactaga ttgcaaaaca    5640
aaaatcccac aggcaatgtt tctacaaaaa ttagatggca atgcacactt tcaccccca    5700 aatatcggag gtaggggtg ccaaatcatc aaccaccgta agatctgcac cgtgtcagca    5760
catgtgtgag aaaagcagag aaacaacaag gtatctgatg cttctgagaa cacgagagct    5820
ctcaaacagc cagcaggtag tcactagata tatagaaggc caggctgaca gcagctgttg    5880
aatctagtag gggtttggcc tagcactcca acaaagctta caagccaggg ctgcctccca    5940
ggagaagatc ctcatactcc tggaagtgga atctaaattg agcaggtcac cagacagatg    6000
t                                                                   6001
```

<210> SEQ ID NO 11
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 11
ccagctgctt ggcgcagacg                                                20

```
<210> SEQ ID NO 12
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 12
gccagaaagc tcaaacttga                                                   20

<210> SEQ ID NO 13
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 13
ccacaagctg tccagtctaa                                                   20

<210> SEQ ID NO 14
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 14
ggtcacactc tcaacaaata                                                   20

<210> SEQ ID NO 15
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 15
aaacatgtaa cttttggtca                                                   20

<210> SEQ ID NO 16
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 16
gggaagagtt gttgtgtgag                                                   20

<210> SEQ ID NO 17
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 17
agggtggagt cgcactggct                                                   20

<210> SEQ ID NO 18
```

```
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 18
acgaaggcga cgcggacggg                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 19
gccgacggcc ggccggctgc                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 20
ggtgcacacg ccgatcttgc                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 21
tctttggcgg tgcacacgcc                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 22
gcaccatctt tggcggtgca                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 23
gcagggagca ccatctttgg                                              20

<210> SEQ ID NO 24
<211> LENGTH: 20
```

```
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 24
aagatgcagg gagcaccatc                                                 20

<210> SEQ ID NO 25
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 25
ccaccgaaga tgcagggagc                                                 20

<210> SEQ ID NO 26
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 26
ccgtaccacc gaagatgcag                                                 20

<210> SEQ ID NO 27
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 27
gtacttgcag ctgctctgga                                                 20

<210> SEQ ID NO 28
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 28
gggcatgcag cccaccgccc                                                 20

<210> SEQ ID NO 29
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 29
aggcccaacc acggtttggt                                                 20

<210> SEQ ID NO 30
<211> LENGTH: 20
<212> TYPE: DNA
```

```
<213> ORGANISM: Artificial Sequence
<220> FEATURE:
<223> OTHER INFORMATION: Antisense directed to human connective tissue
      growth factor (CTGF)

<400> SEQUENCE: 30
agggcaggcc caaccacggt                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 31
taagccgcga gggcaggccc                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 32
cccacaggtc ttggaacagg                                                   20

<210> SEQ ID NO 33
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 33
agatgcccat cccacaggtc                                                   20

<210> SEQ ID NO 34
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 34
ccagtctaat gagttaatgt                                                   20

<210> SEQ ID NO 35
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 35
ttcaagttcc agtctaatga                                                   20

<210> SEQ ID NO 36
<211> LENGTH: 20
<212> TYPE: DNA
<213> ORGANISM: Artificial Sequence
```

-continued

<220> FEATURE:
<223> OTHER INFORMATION: Antisense directed to human connective tissue
      growth factor (CTGF)

<400> SEQUENCE: 36
ttttccccca gttagaaaaa                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 37
cacaatgttt tgaattgggt                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 38
acatggcaca atgttttgaa                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 39
gtttgacatg gcacaatgtt                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 40
tatttgtttg acatggcaca                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 41
tgatagacta tttgtttgac                                              20

<210> SEQ ID NO 42
<211> LENGTH: 20
<212> TYPE: DNA
<213> ORGANISM: Artificial Sequence
<220> FEATURE:

```
<223> OTHER INFORMATION: Antisense directed to human connective tissue
      growth factor (CTGF)

<400> SEQUENCE: 42
gttccactgt caagtcttaa                                                    20

<210> SEQ ID NO 43
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 43
tgtactaatg tagttccact                                                    20

<210> SEQ ID NO 44
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 44
cattctggtg ctgtgtacta                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 45
taatatacat tctggtgctg                                                    20

<210> SEQ ID NO 46
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 46
acaccttaat atacattctg                                                    20

<210> SEQ ID NO 47
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 47
taaagccaca ccttaatata                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense directed to human connective tissue
``` growth factor (CTGF)

<400> SEQUENCE: 48
gtaccctccc actgctccta                                           20

<210> SEQ ID NO 49
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 49
aagatgctat ctgatgatac                                           20

<210> SEQ ID NO 50
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 50
cgtataagat gctatctgat                                           20

<210> SEQ ID NO 51
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 51
aatagcaggc atattactcg                                           20

<210> SEQ ID NO 52
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 52
tacacttcaa atagcaggca                                           20

<210> SEQ ID NO 53
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 53
tcaattacac ttcaaatagc                                           20

<210> SEQ ID NO 54
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 54
ggagaatgca catcctagct                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 55
atggctggag aatgcacatc                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 56
tcttgatggc tggagaatgc                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 57
gaatcagaat gtcagagctg                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 58
cattgaaata tcaaagcatt                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 59
ggctaacatt gaaatatcaa                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

```
<400> SEQUENCE: 60
aattgaggct aacattgaaa                                                 20

<210> SEQ ID NO 61
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 61
gttcagaaat tgaggctaac                                                 20

<210> SEQ ID NO 62
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 62
tatggtgttc agaaattgag                                                 20

<210> SEQ ID NO 63
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 63
ctacctatgg tgttcagaaa                                                 20

<210> SEQ ID NO 64
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 64
tacattctac ctatggtgtt                                                 20

<210> SEQ ID NO 65
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 65
gacaagcttt acattctacc                                                 20

<210> SEQ ID NO 66
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 66
```
gatcagacaa gctttacatt                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 67
atgctttgaa cgatcagaca                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 68
atttcatgct ttgaacgatc                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 69
gtatccattt catgctttga                                           20

<210> SEQ ID NO 70
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 70
ccatataagt atccatttca                                           20

<210> SEQ ID NO 71
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 71
gaatttccat ataagtatcc                                           20

<210> SEQ ID NO 72
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 72
tctgagcaga atttccatat                                                20

<210> SEQ ID NO 73
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 73
tgtcattcta tctgagcaga                                                20

<210> SEQ ID NO 74
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 74
tttgacggac tgtcattcta                                                20

<210> SEQ ID NO 75
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 75
aacaatctgt tttgacggac                                                20

<210> SEQ ID NO 76
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 76
tgatgcctcc cctttgcaaa                                                20

<210> SEQ ID NO 77
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 77
tgccaaggac actgatgcct                                                20

<210> SEQ ID NO 78
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 78
cagcctgcca aggacactga                                                20

<210> SEQ ID NO 79
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 79
gaaatcagcc tgccaaggac                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 80
acctagaaat cagcctgcca                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 81
ttcctaccta gaaatcagcc                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 82
taccacattt cctacctaga                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 83
tgaggctacc acatttccta                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 84
taaaagtgag gctaccacat                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 85
caaatgcttc caggtgaaaa                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 86
tagaaacaaa tgcttccagg                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 87
tcatatcaaa gtagaaacaa                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 88
tccgaaaaac agtcatatca                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 89
acccggctgc agagggcgag                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 90
cgcttacccg gctgcagagg                                               20

```
<210> SEQ ID NO 91
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 91
gacagggcgg tcagcggcgc                                                 20

<210> SEQ ID NO 92
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 92
agtccgagcg gtttcttttt                                                 20

<210> SEQ ID NO 93
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 93
aactcagtcc gagcggtttc                                                 20

<210> SEQ ID NO 94
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 94
aaagaaactc agtccgagcg                                                 20

<210> SEQ ID NO 95
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 95
tggagaaaga aactcagtcc                                                 20

<210> SEQ ID NO 96
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 96
gcagctggag aaagaaactc                                                 20

<210> SEQ ID NO 97
```

<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 97
tggcagcagc tggagaaaga                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 98
agggagcacc atctttggct                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 99
tcacccgcga gggcaggccc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 100
ggaagactcg actcacccgc                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 101
ttagaggaag actcgactca                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 102
accctgactt agaggaagac                                              20

<210> SEQ ID NO 103
<211> LENGTH: 20

```
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 103
tcacgaccct gacttagagg                                                    20

<210> SEQ ID NO 104
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 104
gagaatcacg accctgactt                                                    20

<210> SEQ ID NO 105
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 105
tgggagagaa tcacgaccct                                                    20

<210> SEQ ID NO 106
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 106
ctccctggga gagaatcacg                                                    20

<210> SEQ ID NO 107
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 107
ggtcggcaca gttaggactc                                                    20

<210> SEQ ID NO 108
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 108
cgttcggtcg gcacagttag                                                    20

<210> SEQ ID NO 109
<211> LENGTH: 20
<212> TYPE: DNA
```

```
<213> ORGANISM: Artificial Sequence
<220> FEATURE:
<223> OTHER INFORMATION: Antisense directed to human connective tissue
      growth factor (CTGF)

<400> SEQUENCE: 109
cctggataag gtatttcccc                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 110
acaaacacca tgtaaaacgc                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 111
gagcacacaa acaccatgta                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 112
tgcgagagca gagcacacaa                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 113
taagctgcga gagcagagca                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 114
gtcggtaagc tgcgagagca                                              20

<210> SEQ ID NO 115
<211> LENGTH: 20
<212> TYPE: DNA
<213> ORGANISM: Artificial Sequence
```

```
<220> FEATURE:
<223> OTHER INFORMATION: Antisense directed to human connective tissue
      growth factor (CTGF)

<400> SEQUENCE: 115
ttccagtcgg taagctgcga                                                     20

<210> SEQ ID NO 116
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 116
acatgtacct taatgttctc                                                     20

<210> SEQ ID NO 117
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 117
gcagaacatg taccttaatg                                                     20

<210> SEQ ID NO 118
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 118
taggagcaga acatgtacct                                                     20

<210> SEQ ID NO 119
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 119
gttaatagga gcagaacatg                                                     20

<210> SEQ ID NO 120
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 120
tgaaaaatag ttaataggag                                                     20

<210> SEQ ID NO 121
<211> LENGTH: 20
<212> TYPE: DNA
<213> ORGANISM: Artificial Sequence
<220> FEATURE:
```

```
<223> OTHER INFORMATION: Antisense directed to human connective tissue
      growth factor (CTGF)

<400> SEQUENCE: 121
ccactgtttt tcctgtgaaa                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 122
aagttgggtc ctatccactg                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 123
gccctaagtt gggtcctatc                                                    20

<210> SEQ ID NO 124
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 124
caagagccct aagttgggtc                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 125
cgtggcaaga gccctaagtt                                                    20

<210> SEQ ID NO 126
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 126
cgggcttata ctaacaagcg                                                    20

<210> SEQ ID NO 127
<211> LENGTH: 20
<212> TYPE: DNA
<213> ORGANISM: Artificial Sequence
<220> FEATURE:
<223> OTHER INFORMATION: Antisense directed to human connective tissue
``` growth factor (CTGF)

<400> SEQUENCE: 127
gataacgggc ttatactaac                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 128
ttggagataa cgggcttata                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 129
tagttttgga gataacgggc                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 130
ttagatagtt ttggagataa                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 131
caatggttag atagttttgg                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 132
cagctcaatg gttagatagt                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

```
<400> SEQUENCE: 133
caaaacagct caatggttag                                           20

<210> SEQ ID NO 134
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 134
tccagcaaaa cagctcaatg                                           20

<210> SEQ ID NO 135
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 135
ctcattccag caaaacagct                                           20

<210> SEQ ID NO 136
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 136
aagctctcat tccagcaaaa                                           20

<210> SEQ ID NO 137
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 137
tacacaagct ctcattccag                                           20

<210> SEQ ID NO 138
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 138
ggttgctatt acacaagctc                                           20

<210> SEQ ID NO 139
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)
```

<400> SEQUENCE: 139
ctggtggttg ctattacaca                                              20

<210> SEQ ID NO 140
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 140
gaaaactggt ggttgctatt                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 141
tagtggaaaa ctggtggttg                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 142
ttaactaacc ctgtggaaga                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 143
tgtcttgaat taactaaccc                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 144
tggaatgtct tgaattaact                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 145
gccagagcct ctcttggaat                                          20

<210> SEQ ID NO 146
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 146
aaaaatagcc agagcctctc                                          20

<210> SEQ ID NO 147
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 147
tgtccaaaaa tagccagagc                                          20

<210> SEQ ID NO 148
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 148
tgctatgtcc aaaaatagcc                                          20

<210> SEQ ID NO 149
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 149
tcatttgcta tgtccaaaaa                                          20

<210> SEQ ID NO 150
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 150
gagtctcatt tgctatgtcc                                          20

<210> SEQ ID NO 151
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 151
agtttgagtc tcatttgcta                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 152
gaggaagttt gagtctcatt                                              20

<210> SEQ ID NO 153
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 153
cttctgttgt ctgacttctg                                              20

<210> SEQ ID NO 154
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 154
cctctgtgtt ttagtcttct                                              20

<210> SEQ ID NO 155
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 155
tttcttcaac cctctgtgtt                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 156
ggagtggctt tcttcaaccc                                              20

<210> SEQ ID NO 157
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 157
aggaagacaa gggaaaagag                                              20

```
<210> SEQ ID NO 158
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 158
ttctaaggaa gacaagggaa                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 159
tgcccttcta aggaagacaa                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 160
ggatgcgagt tgggatctgg                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 161
ccagctgctt ggcgcagacg                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 162
gccagaaagc tcaaacttga                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 163
ccacaagctg tccagtctaa                                              20
```

```
<210> SEQ ID NO 164
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 164
ggtcacactc tcaacaaata                                                    20

<210> SEQ ID NO 165
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 165
aaacatgtaa cttttggtca                                                    20

<210> SEQ ID NO 166
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 166
tgacatggca caatgttttg                                                    20

<210> SEQ ID NO 167
<211> LENGTH: 20
<212> TYPE: DNA
<213> ORGANISM: Artificial Sequence
<220> FEATURE:
<223> OTHER INFORMATION: Antisense directed to human connective tissue
      growth factor (CTGF)

<400> SEQUENCE: 167
ccttccctga aggttcctcc                                                    20
```

US 8,772,260 B2

METHODS FOR INHIBITING EXPRESSION OF CONNECTIVE TISSUE GROWTH FACTOR

This application is a divisional of U.S. Ser. No. 12/547,474, filed Aug. 25, 2009, now U.S. Pat. No. 8,252,762 now allowed, claiming benefit of U.S. Provisional Application No. 61/190,121, filed Aug. 25, 2008, the contents of each of which are hereby incorporated in their entireties into this application.

SEQUENCE LISTING

In accordance with 37 C.F.R. 1.52(e)(5), a Sequence Listing in the form of a text file (entitled "706240_ST25.txt," created on Mar. 20, 2013 and 41.84 kb in size) is incorporated by reference in its entirety.

Throughout this application, certain patents and publications are referenced, the latter by authors, journal citation and publication date. The disclosures of these patents and publications in their entireties are hereby incorporated by reference into this application in order to more fully describe the state of the art to which this invention relates.

FIELD OF INVENTION

The present invention relates to novel antisense oligonucleotides (ASOs) useful for treating hyperprolific disorders and fibrotic diseases, and for reducing scarring resulting from wound healing.

BACKGROUND OF THE INVENTION

Antisense technology is emerging as an effective means for reducing the expression of specific gene products and may therefore prove to be uniquely useful in a number of therapeutic, diagnostic, and research applications for the modulation of connective tissue growth factor (CTGF) expression. (See U.S. Pat. No. 6,965,025B2 to Gaarde et al.)

An antisense compound is an oligomeric compound that is capable of undergoing hybridization to a target nucleic acid (e.g. a target mRNA molecule).

Antisense compounds, compositions and methods for modulating expression of CTGF and for treating disease associated with expression of CTGF are disclosed in aforementioned U.S. Pat. No. 6,965,025B2, herein incorporated by reference. However, there remains a need for additional such compounds capable of providing enhanced inhibition of CTGF expression and functions as well as other advantageous properties.

In one embodiment, this invention specifically provides preferred modified antisense oligonucleotides for inhibiting CTGF expression. These have been demonstrated to be significantly, and unexpectedly more potent than previously described ASOs targeting CTGF.

Connective tissue growth factor (CTGF; also known as ctgrofact, fibroblast inducible secreted protein, fisp-12, NOV2, insulin-like growth factor-binding protein-related protein 2, IGFBP-rP2, IGFBP-8, HBGF-0.8, Hcs24, and ecogenin) is a member of the CCN (CTGF/CYR61/NOV) family of modular proteins, named for the first family members identified, connective tissue growth factor, cysteine-rich (CYR61), and nephroblastoma overexpressed (NOV), but the family also includes the proteins ELM-1 (expressed in low-metastatic cells), WISP-3 (Wnt-1-induced secreted protein), and COP-1 (WISP-2). CCN proteins have been found to be secreted, extracellular matrix-associated proteins that regulate cellular processes such as adhesion, migration, mitogenesis, differentiation, survival, angiogenesis, atherosclerosis, chondrogenesis, wound healing, tumorigenesis, and vascular and fibrotic diseases like scleroderma (Lau and Lam, Exp. Cell Res., 1999, 248, 44-57). The connective tissue growth factor protein was shown to stimulate DNA synthesis and promote chemotaxis of fibroblasts (Bradham et al., J. Cell Biol., 1991, 114, 1285-1294).

In most cases, a single 2.4-kilobase CTGF transcript has been reported in expression studies, although 3.5- and 7-kilobase transcripts have been reported in glioblastoma cells. Connective tissue growth factor is expressed in fibroblasts during normal differentiation processes that involve extracellular matrix (ECM) production and remodeling, such as embryogenesis and uterine decidualization following implantation. Connective tissue growth factor is also frequently overexpressed in fibrotic skin disorders such as systemic sclerosis, localized skin sclerosis, keloids, scar tissue, eosinophilic fasciitis, nodular fasciitis, and Dupuytren's contracture. Connective tissue growth factor mRNA or protein levels are elevated in fibrotic lesions of major organs and tissues including the liver, kidney, lung, cardiovascular system, pancreas, bowel, eye, and gingiva. In mammary, pancreatic and fibrohistiocytic tumors characterized by significant connective tissue involvement, connective tissue growth factor is overexpressed in the stromal compartment. In many cases, connective tissue growth factor expression is linked spatially and temporally to the profibrogenic cytokine transforming growth factor-beta (TGF-beta) (Moussad and Brigstock, Mol. Genet. Metab., 2000, 71, 276-292).

Connective tissue growth factor has been mapped to human chromosomal region 6q23.1, proximal to the c-myb gene, and chromosomal abnormalities involving this region have been associated with human tumors, such as Wilms' tumor (Martinerie et al., Oncogene, 1992, 7, 2529-2534).

Tumors with significant fibrotic and vascular components exhibit increased CTGF expression, and CTGF may be involved in the pathogenesis of pediatric myofibroblastic tumors. Of 12 pediatric tumors examined, all showed moderate to intense CTGF expression in tumor cells and/or endothelial cells of the associated vasculature (Kasaragod et al., Pediatr. Dev. Pathol., 2001, 4, 37-45).

Connective tissue growth factor mRNA is also specifically upregulated in malignant human leukemic lymphoblasts from children with acute lymphoblastic leukemia (ALL) (Vorwerk et al., Br. J. Cancer, 2000, 83, 756-760), and both mRNA and protein levels are upregulated by TGF-beta in Hs578T human breast cancer cells in a dose-dependent manner, indicating that CTGF is an important neuroendocrine factor and a critical downstream effector of TGF-beta (Yang et al., J. Clin. Endocrinol. Metab., 1998, 83, 2593-2596).

In a murine lung fibrosis model, an increase in connective tissue growth factor mRNA expression is also induced by bleomycin, a known lung fibrogenic agent (Lasky et al., Am. J. Physiol., 1998, 275, L365-371), as well as in bronchoalveolar lavage cells from patients with idiopathic pulmonary fibrosis and pulmonary sarcoidosis, in comparison to healthy nonsmoking control subjects, indicating that connective tissue growth factor is involved in the fibroproliferative response to injury (Allen et al., Am. J. Respir. Cell Moll. Biol., 1999, 21, 693-700). Similarly, in an experimental model of proliferative glomerulonephritis, connective tissue growth factor mRNA expression was strongly increased in extracapillary and mesangial proliferative lesions and in areas of periglomerular fibrosis. The early glomerular connective tissue growth factor overexpression coincided with a striking upregulation of TGF-beta proteins, and the kinetics of connective tissue growth factor expression strongly suggest a role in glomerular repair, possibly downstream of TGF-beta in this model of transient renal injury (Ito et al., J. Am. Soc. Nephroi., 2001, 12, 472-484).

Disclosed and claimed in U.S. Pat. No. 5,876,730 is a substantially pure or isolated polypeptide characterized as having an amino acid sequence corresponding to the carboxy terminal amino acids of a connective tissue growth factor (CTGF) protein, wherein the polypeptide has an amino acid sequence beginning at amino acid residue 247 or 248 from the N-terminus of connective tissue growth factor, an isolated polynucleotide sequence encoding the connective tissue growth factor polypeptide, a recombinant expression vector which contains said polynucleotide, a host cell containing said expression vector, and a pharmaceutical composition comprising a therapeutically effective amount of connective tissue growth factor polypeptide in a pharmaceutically acceptable carrier. Antisense oligonucleotides are generally disclosed (Brigstock and Harding, 1999).

Disclosed and claimed in U.S. Pat. Nos. 5,783,187; 5,585,270; 6,232,064; 6,150,101; 6,069,006 and PCT Publication WO 00/35936 are an isolated polynucleotide encoding the connective tissue growth factor polypeptide, expression vectors, host cells stably transformed or transfected with said vectors; an isolated polynucleotide comprising 5' untranslated regulatory nucleotide sequences isolated from upstream of connective tissue growth factor, wherein said untranslated regulatory nucleotide sequences comprises a transcriptional and translational initiation region and wherein said sequence is a TGF-beta responsive element; an isolated nucleic acid construct comprising a non-coding regulatory sequence isolated upstream from a connective tissue growth factor (CTGF) gene, wherein said non-coding regulatory sequence is operably associated with a nucleic acid sequence which expresses a protein of interest or antisense RNA, wherein said nucleic acid sequence is heterologous to said non-coding sequence; and a fragment of connective tissue growth factor (CTGF) polypeptide having the ability to induce ECM synthesis, collagen synthesis and/or myofibroblast differentiation, comprising an amino acid sequence encoded by at least exon 2 or exon 3 of said polypeptide. Further claimed is a method for identifying a composition which affects TGF-beta-induced connective tissue growth factor expression, and a method of diagnosing a pathological state in a subject suspected of having a pathology selected from the group consisting of fibrotic disease and atherosclerosis, the method comprising obtaining a sample suspected of containing connective tissue growth factor, whereby detecting a difference in the level of connective tissue growth factor in the sample from the subject as compared to the level of connective tissue growth factor in the normal standard sample is diagnostic of a pathology characterized by a cell proliferative disorder associated with connective tissue growth factor in the subject. Further claimed is a method for ameliorating a cell proliferative disorder associated with connective tissue growth factor, comprising administering to a subject having said disorder, at the site of the disorder, a composition comprising a therapeutically effective amount of an antibody or fragment thereof that binds to connective tissue growth factor, wherein said antibody or fragment thereof does not bind to PDGF. Antisense oligonucleotides are generally disclosed (Grotendorst, 2000; Grotendorst and Bradham, 2001; Grotendorst and Bradham, 2000; Grotendorst and Bradham, 1996; Grotendorst and Bradham, 1998; Grotendorst and Bradham, 2000).

Disclosed and claimed in PCT Publication WO 00/27868 is a substantially pure connective tissue growth factor polypeptide or functional fragments thereof, an isolated polynucleotide sequence encoding said polypeptide, said polynucleotide sequence wherein T can also be U, a nucleic acid sequence complementary to said polynucleotide sequence, and fragments of said sequences that are at least 15 bases in length and that will hybridize to DNA which encodes the amino acid sequence of the connective tissue growth factor protein under moderate to highly stringent conditions. Further claimed is an expression vector including said polynucleotide, a host cell stably transformed with said vector, an antibody that binds to said polypeptide, and a method for producing said polypeptide. Further claimed is a method for inhibiting the expression of connective tissue growth factor in a cell comprising contacting the cell with a polynucleotide which binds to a target nucleic acid in the cell, wherein the polynucleotide inhibits the expression of connective tissue growth factor in the cell, wherein the polynucleotide is an antisense polynucleotide, as well as a kit for the detection of connective tissue growth factor expression comprising a carrier means being compartmentalized to receive one or more containers, comprising at least one container containing at least one antisense oligonucleotide that binds to connective tissue growth factor (Schmidt et al., 2000).

Disclosed and claimed in PCT Publication WO 00/13706 is a method for treating or preventing fibrosis, the method comprising administering to a subject in need an effective amount of an agent that modulates, regulates or inhibits the expression or activity of connective tissue growth factor or fragments thereof, and wherein the agent is an antibody, an antisense oligonucleotide, or a small molecule. The method is directed to treating kidney fibrosis and associated renal disorders, in particular, complications associated with diabetes and hypertension (Riser and Denichili, 2000).

Disclosed and claimed in PCT Publication WO 01/29217 is an isolated nucleic acid molecule comprising a nucleic acid sequence encoding a polypeptide comprising an amino acid sequence selected from a group comprising NOV1, NOV2 (connective tissue growth factor), and NOV3, a mature form or variant of an amino acid sequence selected from said group, as well as a nucleic acid molecule comprising a nucleic acid sequence encoding a polypeptide comprising an amino acid sequence selected from said group as well as mature and variant forms or fragments of said polypeptides, and the complement of said nucleic acid molecule. Antisense oligonucleotides are generally disclosed (Prayaga et al., 2001).

Hypertrophic scar formation, in particular, is a major clinical problem in the resolution of severe burns and can give rise to exuberant scarring that result in permanent functional loss and the stigma of disfigurement. Annually, over 1 million people require treatment for burns in the United States. The incidence of hypertrophic scarring following burns is a common outcome that creates a problem of enormous magnitude. Therefore an inhibitor of CTGF such as an antisense oligonucleotide (ASO) should be highly effective in preventing the severity of hypertrophic scars subsequent to burns. This activity could be evaluated by applying formulated ASO topically and monitoring the severity of the developed scar subsequent to occurring of the burn.

CTGF may be an attractive target for modulating hypertrophic scarring for several reasons. As a cofactor and downstream mediator of TGF-β1 or TGF-β2, CTGF may represent a more specific target than TGF-β1 or TGF-β2 for gene-directed molecular therapies aimed at scarring, particularly since TGF-β1 or TGF-β2 has pluripotent effects unrelated to scar formation. In addition, CTGF may have TGF-β1 or TGF-β2 independent functions in maintaining a fibrotic phenotype that would be neglected by anti-TGF-β1 or TGF-β2 strategies. Despite advances in understanding CTGF's roles in augmenting fibrosis in multiple organ systems and in chronic dermal diseases such as scleroderma, CTGF's roles in acute scarring and wound healing remain largely observational.

Currently, there are no known therapeutic agents which effectively inhibit the synthesis of connective tissue growth factor and to date, investigative strategies aimed at modulating connective tissue growth factor function have involved the use of sodium butyrate (NaB), function blocking antibodies and antisense oligonucleotides.

Dietary factors are believed to play an important role in both the development and prevention of human cancers, including breast carcinoma. The dietary micronutrient NaB is a major end product of digestion of dietary starch and fiber, and is a potent growth inhibitor that initiates cell differentiation of many cell types in vitro. NaB exerts its biological effects, in part, as a histone deacetylase inhibitor in mammary epithelial cells, induces apoptotic cell death in Hs578T estrogen-non-responsive human breast cancer cells, and can activate different genes involved in cell cycle arrest depending on cell type. NaB specifically upregulates the expression of connective tissue growth factor in a dose-dependent manner, stimulating an increase in both mRNA and protein levels in both cancerous and non-cancerous mammary cells (Tsubaki et al., J. Endocrinol., 2001, 169, 97-110).

TGF-beta has the unique ability to stimulate growth of normal fibroblasts in soft agar, a property of transformed cells. Connective tissue growth factor cannot induce these anchorage-independent growth normal rat kidney (NRK) fibroblasts, but connective tissue growth factor synthesis and action are essential for TGF-beta-induced anchorage-independence. Antibodies to connective tissue growth factor specifically blocked TGF-beta-induced anchorage-independent growth, and NRK fibroblasts transformed with a construct expressing the connective tissue growth factor gene in the antisense orientation were not responsive to TGF-beta in the anchorage-independent growth assay (Kothapalli et al., Cell Growth. Differ., 1997, 8, 61-68). These CTGF-antisense expressing NRK cells were also used to show that TGF-beta-stimulated collagen synthesis is mediated by connective tissue growth factor, indicating that connective tissue growth factor may be a useful target for antifibrotic therapies (Duncan et al., Faseb J., 1999, 13, 1774-1786).

The 3'-untranslated region (UTR) of the human connective tissue growth factor cDNA bears several consensus sequences for regulatory elements. When the 3'-UTR was fused downstream of a reporter gene, it was found to act as a strong cis-acting repressive element, and the antisense 3'-UTR had a similar, but stronger effect. (Kubota et al., FEBS Lett., 1999, 450, 84-88). Comparison of the human and mouse connective tissue growth factor 3'-UTRs revealed a conserved small segment of 91 bases. This region was amplified by RT-PCR from NIH3T3 mouse fibroblasts and used to make a chimeric fusion construct for analysis of its repressive effects. The mouse connective tissue growth factor 3'-UTR in either the sense or the antisense orientation had a strong repressive effect on transcription of the reporter gene, indicating an orientation independence of this regulatory element (Kondo et al., Biochem. Biophys. Res. Commun., 2000, 278, 119-124).

A phosphorothioate antisense oligonucleotide, 16 nucleotides in length and targeted to the translation initiation start site, was used to inhibit expression of connective tissue growth factor and suppress proliferation and migration of bovine aorta vascular endothelial cells in culture (Shimo et al., J. Biochem. (Tokyo), 1998, 124, 130-140). This antisense oligonucleotide was also used to show that connective tissue growth factor induces apoptosis in MCF-7 human breast cancer cells and that TGF-beta-induced apoptosis is mediated, in part, by connective tissue growth factor (Hishikawa et al., J. Biol. Chem., 1999, 274, 37461-37466). The same antisense oligonucleotide was also found to inhibit the TGF-beta-mediated activation of caspase 3 and thus to inhibit induction of TGF-beta-mediated apoptosis in human aortic smooth muscle cells (HASC) (Hishikawa et al., Eur. J. Pharmacol., 1999, 385, 287-290). This antisense oligonucleotide was also used to block connective tissue growth factor expression and demonstrate that high blood pressure upregulates expression of connective tissue growth factor in mesangial cells, which in turn enhances ECM protein production and induces apoptosis, contributing to the remodeling of mesangium and ultimately glomerulosclerosis (Hishikawa et al., J. Biol. Chem., 2001, 276, 16797-16803).

Consequently, there remains a long felt need for additional agents capable of effectively inhibiting connective tissue growth factor function.

SUMMARY OF THE INVENTION

This invention provides compounds which comprise modified oligonucleotides comprising 12-30 linked nucleosides, preferably comprising 20 or at least 12 linked nucleosides, more preferably at least 14 linked nucleosides, of which is capable of inhibitory expression of connective tissue factor. Pharmaceutical and other compositions comprising the antisense compounds of the invention are also provided.

Further provided are methods of treating an animal, particularly a human, having a disease or condition associated with CTGF by administering an amount of such compounds effective to inhibit expression of CTGF, wherein the disease or condition is a hyperprolific disorder, such as cancer and fibrotic diseases. Further provided is a method of reducing scarring resulting from wound healing by administering an amount of such compounds effective to inhibit expression of CTGF.

BRIEF DESCRIPTION OF THE FIGURES

FIG. 7A identifying the 8 exon targeting antisense oligonucleotides and FIG. 7B provides preferred sequences of the antisense oligonucleotides.

DETAILED DESCRIPTION OF THE INVENTION

In one embodiment, this invention provides a compound which comprises a modified oligonucleotide consisting of 12-30 linked nucleosides, at least a 12 nucleobase sequence portion of which is present within the region selected from nucleotides 718-751, 1388-1423, 1457-1689, 2040-2069, 2120-2147, 2728-2797, 2267-2301, 553-611, 1394-1423, 1469-1508, 1559-1605, 1659-1689, 2100-2129 and 1399-1423 of SEQ ID NO: 9.

In another embodiment, this invention provides a compound which comprises a modified oligonucleotide consisting of 12-30 linked nucleosides, at least a 12 nucleobase sequence portion of which is present within the region selected from nucleotides 2540-2559, 2568-2587, 2623-2647 and 2623-2642 of SEQ ID NO: 10.

In one embodiment, this invention provides a compound which comprises a modified oligonucleotide comprising 12-30 linked nucleosides, at least a 12 nucleobase sequence portion of which is present within nucleobase sequences set forth in SEQ ID NOs: 28, 30, 39, 40, 43, 44, 45, 50, 51, 52, 56, 78, 125 and 166.

In a preferred embodiment of the invention, the compound comprises 20 or at least 12 linked nucleosides, more preferably at least 14 linked nucleosides, of which is present within the nucleobase sequences set forth in SEQ ID NOs: 28, 30, 39, 40, 43, 44, 45, 50, 51, 52, 56, 78, 125 and 166.

Figure 1:
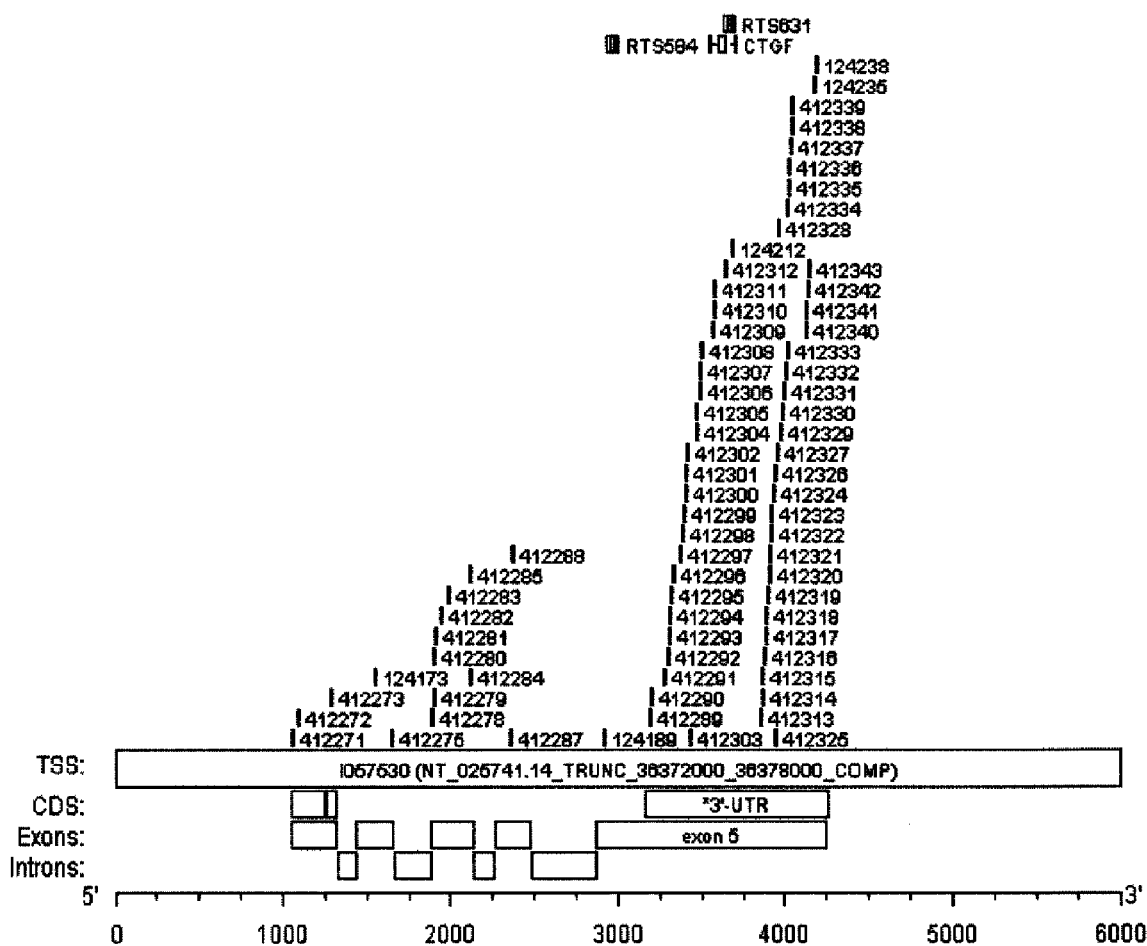
FIG. 1 shows the targeted segments or regions on the CTGF genomic sequence, primarily exon targeted segments, against which antisense oligonucleotides to CTGF were made.
Figure 2:
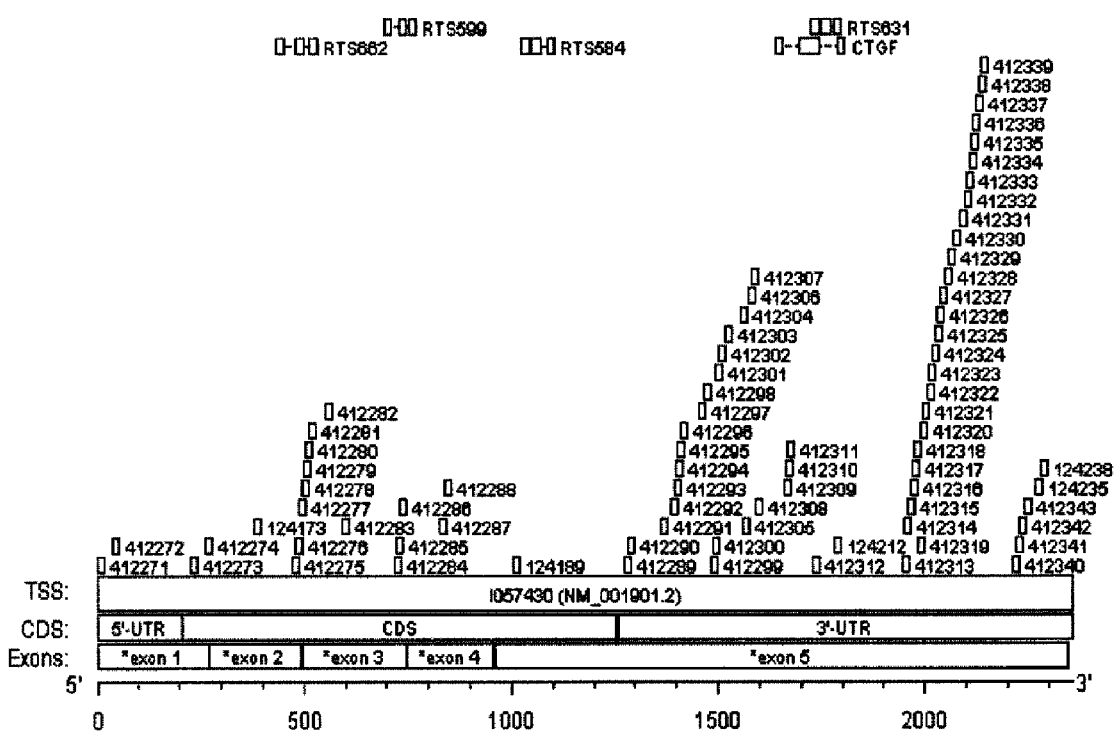
FIG. 2 shows the targeted segments or regions on the CTGF mRNA sequence against which antisense oligonucleotides to CTGF were made.
Figure 3:
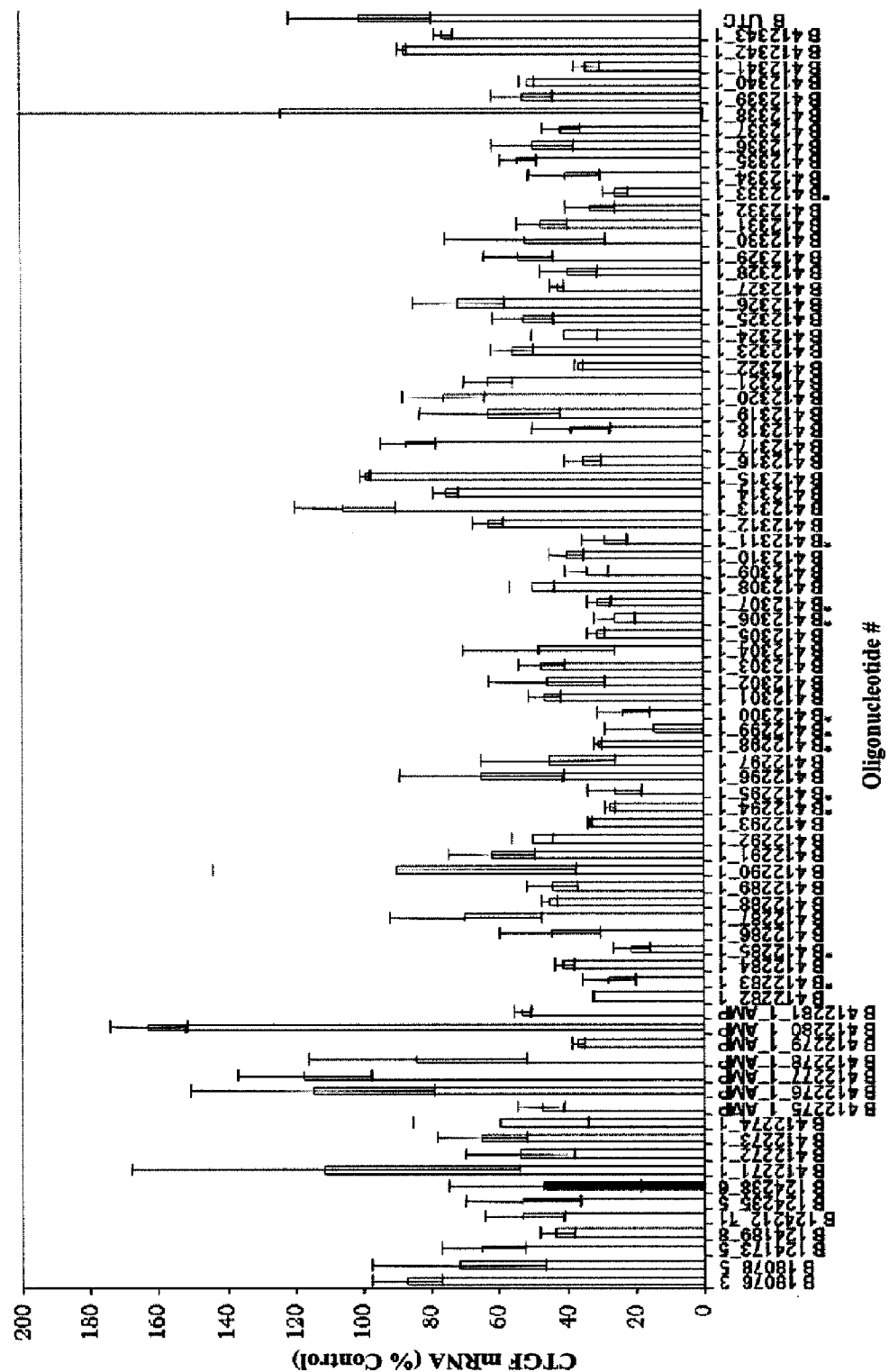
FIG. 3 provides a graphical representation of the testing of antisense oligonucleotides targeting exon sequences on the CTGF mRNA sequence for inhibition of CTGF expression.
Figure 4:
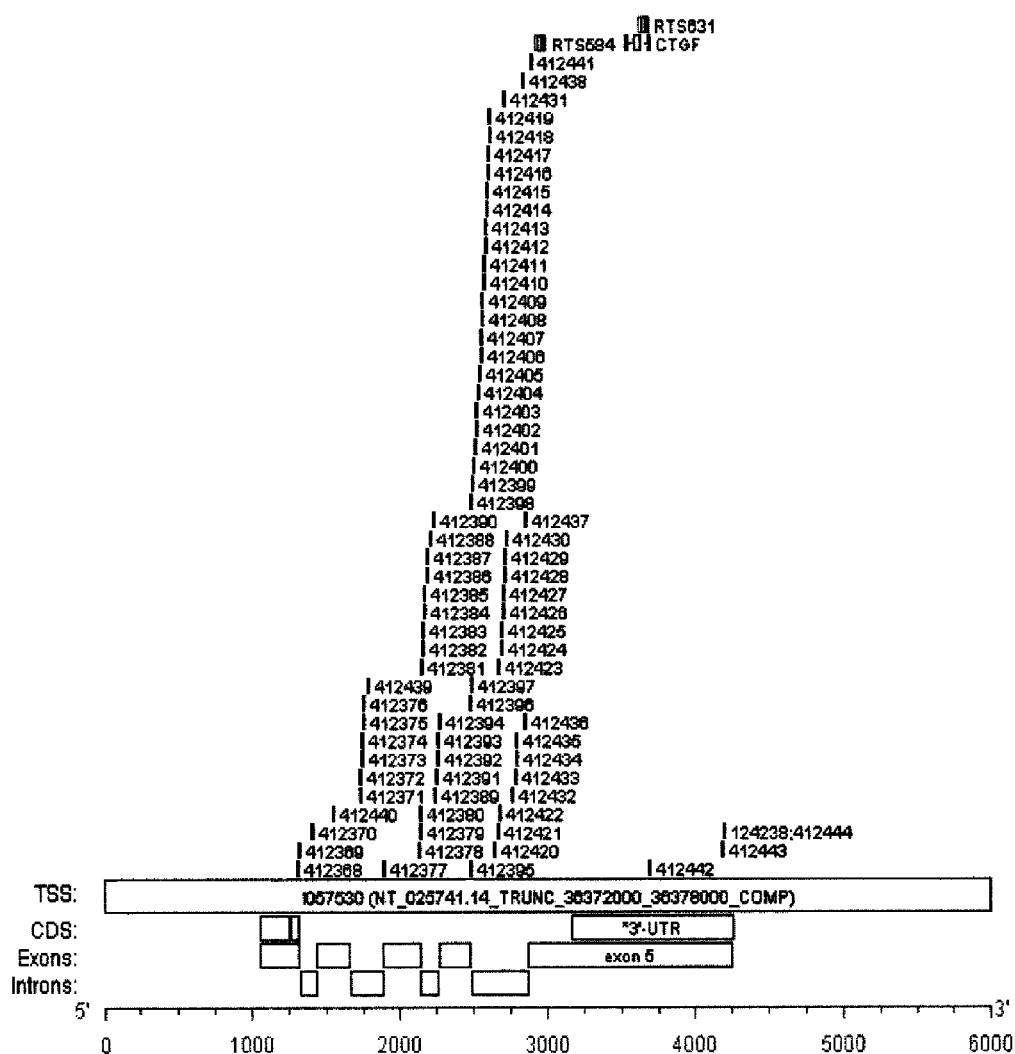
FIG. 4 shows the target segments or regions on the CTGF genomic sequence, primarily intron targeted segments, against which antisense oligonucleotide to CTGF were made.
Figure 5:
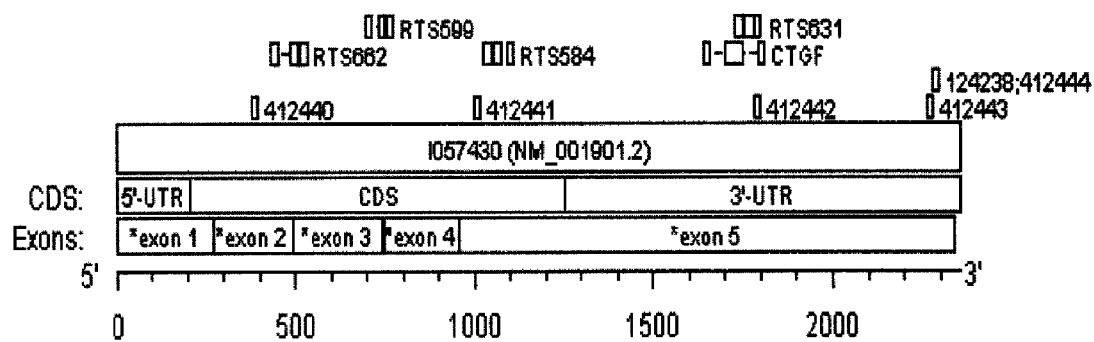
FIG. 5 shows the target segments or regions on the CTGF mRNA sequence against which antisense oligonucleotide to CTGF were made.
Figure 6:
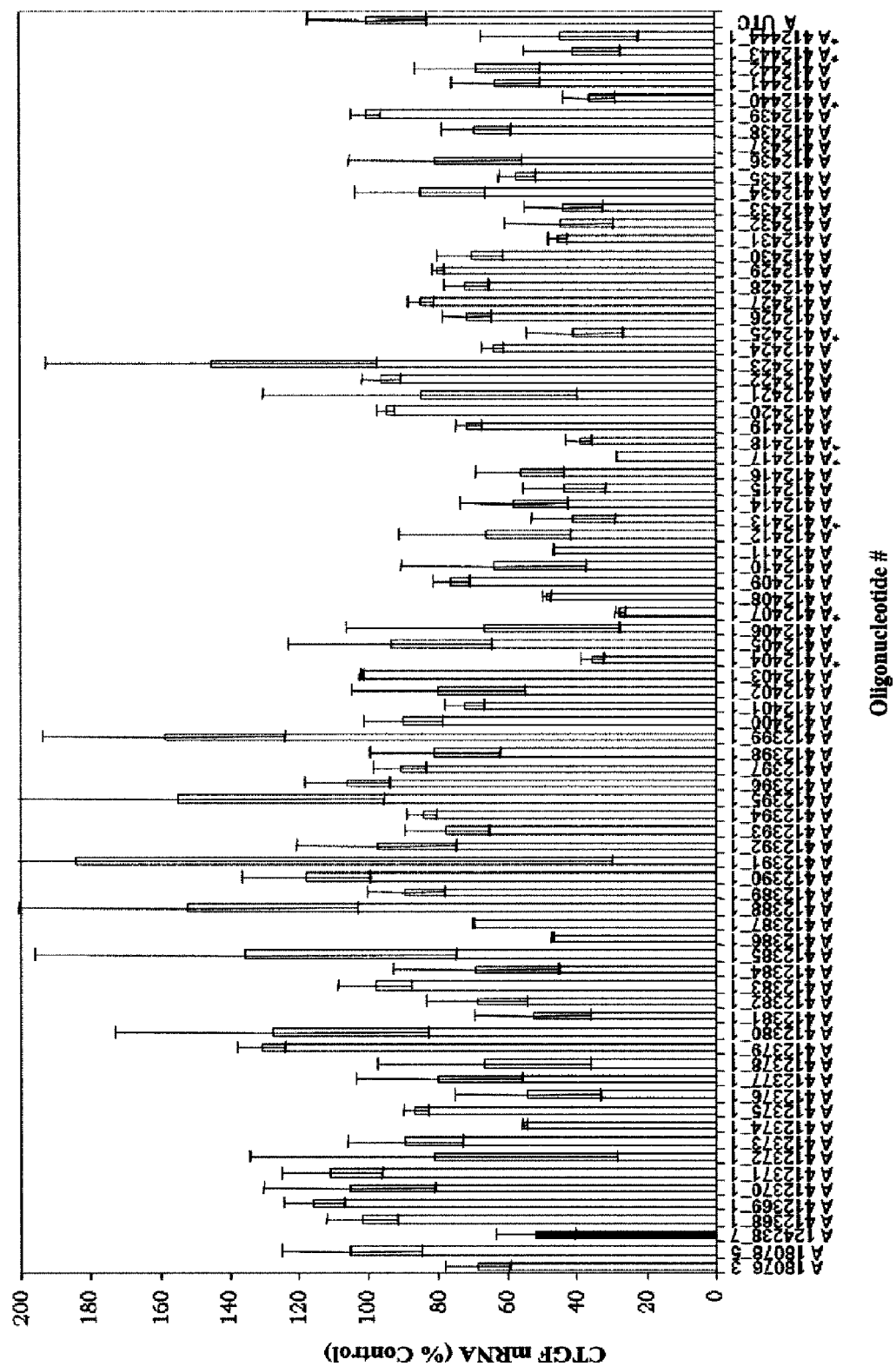
FIG. 6 provides a graphical representation of the result of testing of antisense oligonucleotides targeting primarily intron sequences on the CTGF mRNA sequence for inhibition against CTGF expression.
Figures 7A, 7B:
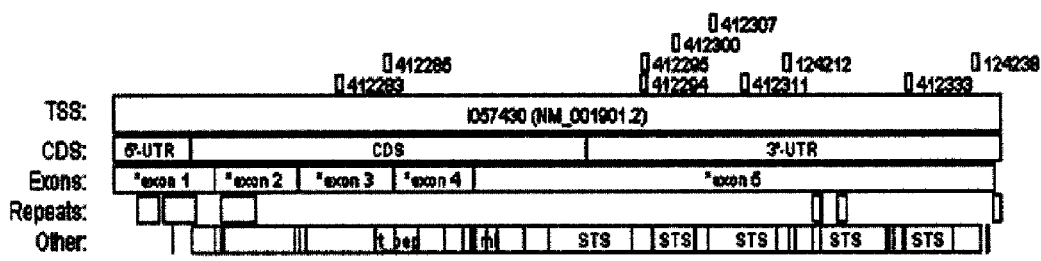
FIGS. 7A and 7B shows the highly active antisense oligonucleotides against CTGF and compares their activity to that of two previously designed antisense oligonucleotides (ISIS 124238 and ISIS 124212) disclosed in U.S. Pat. No. 6,965, 025 B2.
Figure 8:
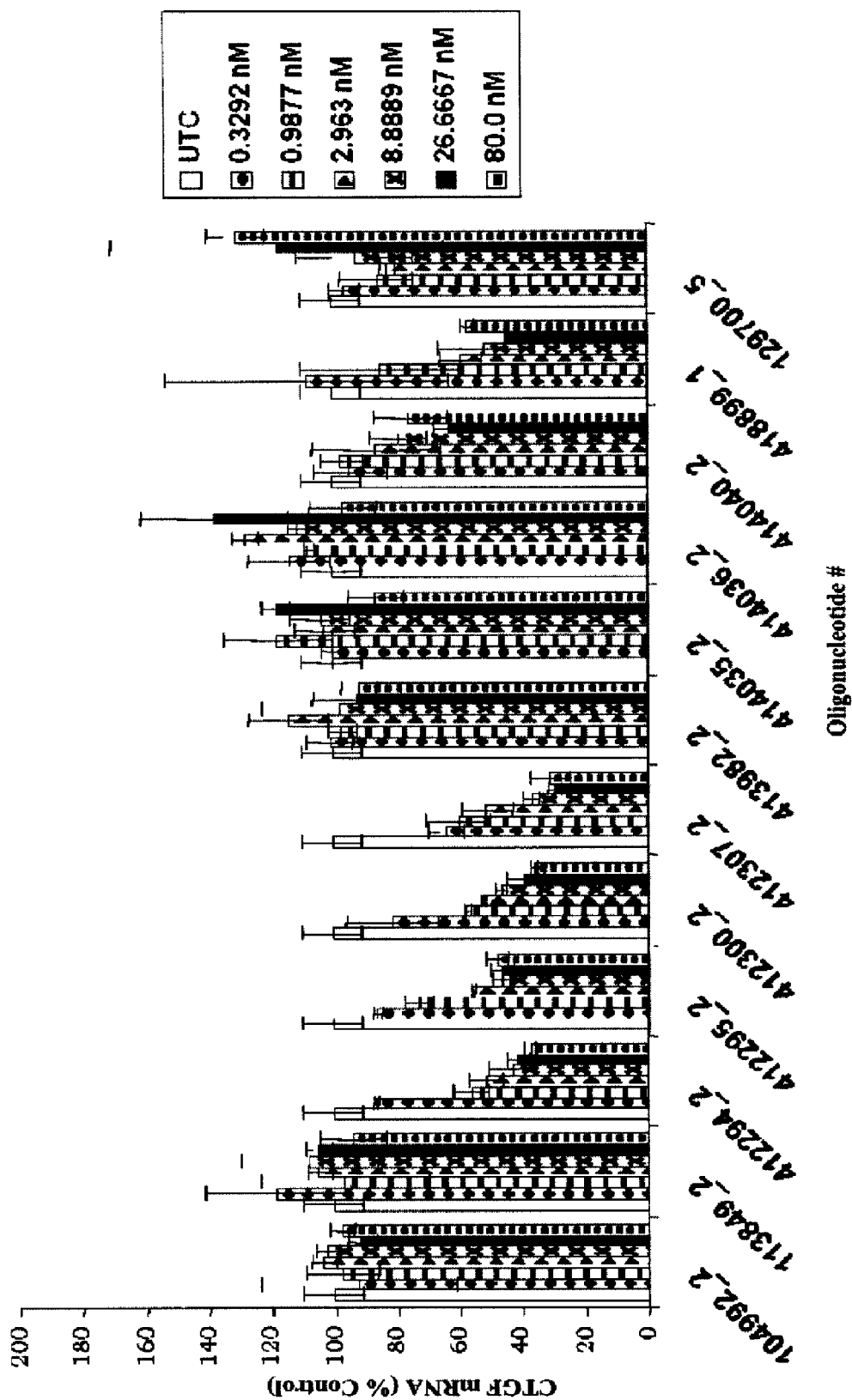
FIG. 8 provides a graphical representation of the dose response obtained for the nine highly active novel lead antisense sequences of human CTGF for inhibiting CTGF expression in cultured human umbilical vein endothelial cells. Sequence 141923 is a negative control, and Sequences 124238 and 124212 are two previously designed sequences.

The selection of these sequences was determined by screening results presented in FIGS. 1 to 7B as well as results from a dose response study in human umbilical vein endothelial cells (HuVEC) (FIG. 8). Details of the experiment and data are provided in Example 8 in the Example Section below.

The target sequences presented in FIGS. 1 to 6 include both intron and exon targeting sequences. A target region is a structurally defined region of the nucleic acid. For example, a target region may encompass a 3' UTR, a 5' UTR, an exon, an intron, a coding region, a translation initiation region, translation termination region, or other defined nucleic acid region. Targeting includes determination of at least one target segment to which an antisense compound hybridizes, such that a desired effect occurs. In this embodiment, the desired effect is a reduction in mRNA target nucleic acid levels.

Multiple sequences with apparent activity greater than previously designed sequences such as SEQ ID 15 (Isis 124238), were identified in both exonic and intronic sequences. A number of new intronic (SEQ NO. 125) and exonic (SEQ NOs. 28, 30, 40, 45, 52, 50 and 78) oligonucleotides appear to be significantly more active than other sequences.

SEQ ID NOs. 39 and 40 were shown to be highly effective inhibitors of CTGF expression in the original ASO screen for activity (data shown here). To further examine whether this area on the CTGF mRNA represents a "hot spot" to target with ASOs, an additional ASO sequence (SEQ ID NO 166) was designated, which is designed to hybridize to sequence just upstream of those targeted by SEQ NOs. 39 and 40. This ASO (SEQ ID NO. 166) was also found to be a highly potent inhibitor of CTGF mRNA expression, demonstrating that this section of the CTGF mRNA is an attractive region to target with ASO inhibitors.

In a certain embodiment the antisense compound is complimentary to a portion of the region of CTGF targeted by active oligonucleotides which stretches from target sites 1396 through 1424. This is the sequence space targeted by Isis 418899, 412295 and 412294 (SEQ ID NOs: 166, 40 and 39, respectively).

This invention also provides a compound which comprises a modified oligonucleotide comprising at least 12, preferably at least 14, linked nucleosides, the nucleobase sequence of which is a portion of one of the nucleobase sequences set forth in SEQ ID NOs: 28, 30, 39, 40, 43, 44, 45, 50, 51, 52, 56, 78, 125 and 166.

The antisense compounds described herein can comprise an oligonucleotide having 12 to 30, 12 to 20, and preferably 14 to 20 linked nucleosides.

In one embodiment of the invention, the modified oligonucleotide is a single-stranded or a double-stranded oligonucleotide.

The present invention employs oligomeric compounds, particularly antisense oligonucleotides, for use in modulating the function of nucleic acid molecules encoding connective tissue growth factor, ultimately modulating the amount of connective tissue growth factor produced. This is accomplished by providing antisense compounds which specifically hybridize with one or more nucleic acids encoding connective tissue growth factor. As used herein, the terms "target nucleic acid" and "nucleic acid encoding connective tissue growth factor" encompass DNA encoding connective tissue growth factor, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA.

The overall effect of such interference with target nucleic acid function is modulation of the expression of connective tissue growth factor. In the context of the present invention, "modulation" means either an increase (stimulation) or a decrease (inhibition) in the expression of a gene. In the context of the present invention, inhibition is the preferred form of modulation of gene expression and mRNA is a preferred target.

Target Nucleic Acids, Target Regions and Nucleotide Sequences

It is preferred to target specific nucleic acids for antisense. "Targeting" an antisense compound to a particular nucleic acid, in the context of this invention, is a multistep process.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In one embodiment, a target region is a structurally defined region of the nucleic acid. For example, a target region may encompass a 3' UTR, a 5' UTR, an exon, an intron, a coding region, a translation initiation region, translation termination region, or other defined nucleic acid region. The structurally defined regions for the nucleic acid can be obtained by accession number from sequence databases such as NCBI and such information is incorporated herein by reference. In other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In other embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In one embodiment, target segments within a target region are separated by no more than about 300 nucleotides. In other embodiments, target segments within a target region are separated by no more than about, 250, 200, 150, 100, 90, 80, 70, 60, 50, 40, 30, 20, or 10 nucleotides on the target nucleic acid. In another embodiment, target segments within a target region are separated by no more than about 5 nucleotides on the target nucleic acid. In additional embodiments, target segments are contiguous.

Suitable target segments may be found within a 5' UTR, a coding region, a 3' UTR, an intron, or an exon. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In one embodiment, reductions in CTGF mRNA levels are indicative of inhibition of CTGF expression. Reductions in levels of a CTGF protein are also indicative of inhibition of target mRNA expression. Further, phenotypic changes are indicative of inhibition of CTGF expression. For example, an increase in measures of CTGF is indicative of inhibition of CTGF expression.

In detail, the targeting process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding connective tissue growth factor. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding connective tissue growth factor, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, FEDS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in (To, Comb. Chem. High Throughput Screen, 2000, 3, 235-41).

Antisense Compounds

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics.

Antisense compound means an oligomeric compound capable of undergoing hybridization to a target nucleic acid through hydrogen bonding. Antisense compounds include, but are not limited to oligonucleotides, oligonucleosides, oligonucleotide analogs, oligonucleotide mimetics, antisense oligonucleotides, siRNA, RNAi, ribozymes, external guide sequence (EGS) oligonucleotides (oligozymes), and other oligonucleotides which hybridize to the target nucleic acid and modulate its expression.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a nucleic acid is 12 to 30 subunits in length. In other words, antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In one preferred embodiment of the invention, the compound comprises 20 or at least 14 linked nucleosides, wherein the modified oligonucleotide has a sequence which is 100% identical to one of the sequences set forth in SEQ ID NOs: 28, 30, 39, 40, 45, 52, 56, 78, 125 and 166. In another preferred embodiment, the lead compound of interest has the sequence set forth in SEQ ID No: 39 (ISIS 412294).

In certain embodiments, a shortened or truncated antisense compound targeted to a nucleic acid has a single subunit deleted from the 5' end (5' truncation), or alternatively from the 3' end (3' truncation). A shortened or truncated antisense compound targeted to a nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Bhanot et al. (PCT/US2007/068401) provided short antisense compounds, including compounds comprising chemically-modified high-affinity monomers 8 to 16 monomers in length. These short antisense compounds were shown to be useful for reducing target nucleic acids and/or proteins in cells, tissues, and animals with increased potency and improved therapeutic index. Short antisense compounds were effective at lower doses than previously described antisense compounds, allowing for a reduction in toxicity and cost of treatment. In addition, the described short antisense compounds have greater potential for oral dosing.

Hybridizations

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds.

In some embodiments, hybridization occurs between an antisense compound disclosed herein and a nucleic acid. The most common mechanism of hybridization involves hydrogen bonding between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In one embodiment, the antisense compounds provided herein are specifically hybridizable with a nucleic acid.

Complementarity

"Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a CTGF nucleic acid).

Non-complementary nucleobases between an antisense compound and a CTGF nucleic acid may be tolerated provided that the antisense compound remains able to specifically hybridize to a target nucleic acid. Moreover, an antisense compound may hybridize over one or more segments of a CTGF nucleic acid such that intervening or adjacent segments are not involved in the hybridization event (e.g., a loop structure, mismatch or hairpin structure).

In some embodiments, the antisense compounds provided herein are at least 70%, at least 75%, at least 80%, at least 85%, at least 90%, at least 95%, at least 96%, at least 97%, at least 98% or at least 99% complementary to a CTGF nucleic acid. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In other embodiments, the antisense compounds provided herein are fully complementary (i.e. 100% complementary) to a target nucleic acid. For example, antisense compound may be fully complementary to a CTGF nucleic acid, or a target region, or a target segment or target sequence thereof. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In one embodiment, antisense compounds up to 20 nucleobases in length comprise no more than 4, no more than 3, no more than 2 or no more than 1 non-complementary nucleobase(s) relative to a target nucleic acid, such as a CTGF nucleic acid.

In another embodiment, antisense compounds up to 30 nucleobases in length comprise no more than 6, no more than 5, no more than 4, no more than 3, no more than 2 or no more than 1 non-complementary nucleobase(s) relative to a target nucleic acid, such as a CTGF nucleic acid.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In one embodiment, the antisense compounds are complementary to at least an 8 nucleobase portion of a target segment. In another embodiment, the antisense compounds are complementary to at least a 12 nucleobase portion of a target segment. In yet another embodiment, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

In a certain embodiment of the invention, modifications to antisense compounds encompass substitutions or changes to internucleoside linkages, sugar moieties, or nucleobases.

In one embodiment of the invention the compound comprises at least one modification selected from the group consisting of a modified internucleoside linkage, a modified sugar, and a modified nucleobase.

Although antisense oligonucleotides containing a variety of modified internucleoside linkages may be employed, the currently preferred modified internucleoside linkage is a phosphothioate linkage between one or more of the nucleosides or wherein all of the internucleoside linkages are phosphothioate internucleoside linkages. In general, it is also preferred that the antisense oligonucleotide contains at least one and typically more than one modified sugar, wherein the sugar is a bicyclic sugar. Although various modified sugars may be employed it is presently preferred to employ a 2'-O-methoxyethyl sugar.

Further, at least one and typically more than one of the nucleobases contained in the antisense oligonucleotide will be a modified nucleotide such as a 5-methylcytosine.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleotide Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, antisense compounds targeted to a CTGF nucleic acid comprise one or more modified internucleoside linkages. In some embodiments, the modified internucleoside linkages are phosphorothioate linkages. In other embodiments, each internucleoside linkage of an antisense compound is a phosphorothioate internucleoside linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugar Moieties

Modified oligonucleotides may also contain one or more substituted sugar moieties. For example, the furanosyl sugar ring can be modified in a number of ways including substitution with a substituent group, bridging to form a bicyclic nucleic acid "BNA" and substitution of the 4'-0 with a heteroatom such as S or N(R) as described in U.S. Pat. No. 7,399,845 to Seth et al., hereby incorporated by reference herein in its entirety. Other examples of BNAs are described in published International Patent Application No. WO 2007/146511, hereby incorporated by reference herein in its entirety.

Antisense compounds of the invention can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O(CH2)2-OCH3 (2'-O-methoxyethyl or 2'-MOE) substituent group; and bicyclic modified sugars (BNAs), having a 4'-(CH2)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

In some embodiments, the bicyclic sugar moiety is bridged between the 2' and 4' carbon atoms with a biradical group selected from —O—$(CH_2)$p-, —O—$CH_2$—, —O—$CH_2CH_2$—, —O—CH (alkyl)-, —NH—$(CH_2)$p-, —N(alkyl)-$(CH_2)$p-, —O—CH(alkyl)-, —(CH(alkyl))-$(CH_2)$p-, —NH—O—$(CH_2)$p-, —N(alkyl)-O—$(CH_2)$p-, or —O—N(alkyl)-$(CH_2)$p-, wherein p is 1, 2, 3, 4 or 5 and each alkyl group can be further substituted. In certain embodiments, p is 1, 2 or 3.

In one aspect, each of said bridges is, independently, —[C(R1)(R2)]n-, —[C(R1)(R2)]n-O—, —C(R1R2)-N(R1)-O— or —C(R1R2)-O—N(R1)-. In another aspect, each of said bridges is, independently, 4'-$(CH_2)_3$-2', 4'-$(CH_2)_2$-2', 4'-CH$_2$—O-2', 4'-(CH$_2$)$_2$—O-2', 4'-CH$_2$—O—N(R1)-2' and 4'-CH$_2$—N(R1)-O-2'- wherein each R1 is, independently, H, a protecting group or C1-C12 alkyl.

In nucleotides having modified sugar moieties, the nucleobase moieties (natural, modified or a combination thereof) are maintained for hybridization with an appropriate nucleic acid target.

In one embodiment, antisense compounds targeted to a nucleic acid comprise one or more nucleotides having modified sugar moieties. In a preferred embodiment, the modified sugar moiety is 2'-MOE. In other embodiments, the 2'-MOE modified nucleotides are arranged in a gapmer motif.

Currently preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O— —CH$_2$— —O— —CH$_2$— —N(CH$_2$)$_2$. A further preferred modification includes bicyclic nucleic acid (also referred to as locked nucleic acids (LNAs)) in which the 2'-hydroxyl group is linked to the 3' or 4' carbon atom of the sugar ring thereby forming a bicyclic sugar moiety. The linkage is preferably a methelyne (— —CH$_2$——)$_n$ group bridging the 2' oxygen atom and the 4' carbon atom wherein n is 1 or 2 including α-L-Methyleneoxy (4'-CH2-O-2') BNA, β-D-Methyleneoxy (4'-CH2-O-2') BNA and Ethyleneoxy (4'-(CH2)2-O-2') BNA. Bicyclic modified sugars also include (6'S)-6' methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C, 4'-C-oxymethylene linkage thereby forming a bicyclic sugar moiety. The linkage may be a methelyne (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Other preferred bridge groups include the 2'-deoxy-2'-CH$_2$OCH$_2$-4' bridge. LNAs and preparation thereof are described in published International Patent Application Nos. WO 98/39352 and WO 99/14226.

Other preferred modifications include 2'-methoxy (2'-O—CH$_3$), 2'-aminopropoxy (2'OCH$_2$CH$_2$CH$_2$NH$_2$), 2'-allyl (2'—CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics or surrogates (sometimes referred to as DNA analogs) such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety. In certain embodiments, nucleosides are modified by replacement of the ribosyl ring with a surrogate ring system such as a morpholino ring, a cyclohexenyl ring, a cyclohexyl ring or a tetrahydropyranyl ring such as one having one of the formula:

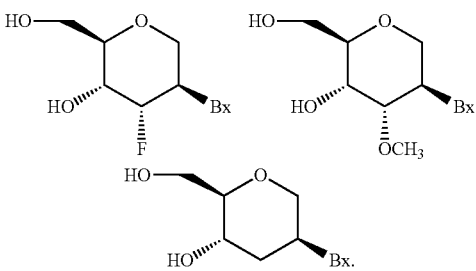

Many other bicyclo and tricyclo sugar surrogate ring systems are also know in the art that can be used to modify nucleosides for incorporation into antisense compounds (see for example review article: Leumann, Christian J.). Such ring systems can undergo various additional substitutions to enhance activity.

In one embodiment of the invention, the compound comprising at least one tetrahydropyran modified nucleoside wherein a tetrahydropyran ring replaces the furanose ring.

In another embodiment of the invention, wherein each of the at least one tetrahydropyran modified nucleoside has the structure:

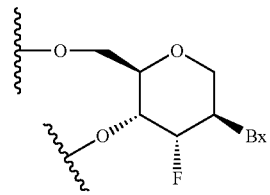

wherein Bx is an optionally protected heterocyclic base moiety.

Modified Nucleobases

Oligonucleotides may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C \equiv C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In one embodiment, antisense compounds targeted to a CTGF nucleic acid comprise one or more modified nucleobases. In an additional embodiment, gap-widened antisense oligonucleotides targeted to a CTGF nucleic acid comprise one or more modified nucleobases. In some embodiments, the modified nucleobase is 5-methylcytosine. In further embodiments, each cytosine is a 5-methylcytosine.

As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C \equiv C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which has an owner in common with the owners of the instant application and also herein incorporated by reference.

Antisense Compound Motifs

In certain embodiment of the invention, the compound comprises a modified oligonucleotide comprised of (a) a gap segment consisting of linked deoxynucleosides, preferably consists of a thirteen linked modified deoxynucleosides; (b) a 5' wing segment consisting of linked modified nucleosides, preferably consists of two linked modified nucleosides; and (c) a 3' wing segment consisting of linked modified nucleosides, preferably consists of five linked nucleosides; wherein the gap segment is positioned between the 5' wing segment and the 3' wing segment, and wherein each modified nucleoside within each wing segment comprises a modified sugar, preferably comprises a 2'-O-methoxyethyl sugar; and wherein each internucleoside linkage is a phosphothioate linkage. These patterns of modified nucleotides in an antisense compound are called motif. These motifs, confer to the antisense compounds properties such to enhance the inhibitory activity, increase binding affinity for a target nucleic acid, or increase resistance to degradation by in vivo nucleases.

In certain embodiments, antisense compounds targeted to a CTGF nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In a preferred embodiment, the regions of a gapmer are differentiated by the types of sugar moieties comprising each distinct region. The types of sugar moieties that are used to differentiate the regions of a gapmer may in some embodiments include β-D-ribonucleosides, β-D-deoxy-ribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 2-13-5, 5-10-5, 4-8-4, 4-12-3, 4-12-4, 3-14-3, 2-16-2, 1-18-1, 3-10-3, 2-10-2, 1-10-1 or 2-8-2.

In some embodiments, the antisense compound as a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10 or 8-2.

In one embodiment, antisense compounds targeted to a nucleic acid possess a 5-10-5 gapmer motif.

In some embodiments, an antisense compound targeted to a nucleic acid has a gap-widened motif. In other embodiments, an antisense oligonucleotide targeted to a nucleic acid has a gap-widened motif.

In one embodiment, a gap-widened antisense oligonucleotide targeted to a nucleic acid has a gap segment of fourteen 2'-deoxyribonucleotides positioned between wing segments of three chemically modified nucleosides. In one embodiment, the chemical modification comprises a 2'-sugar modification. In another embodiment, the chemical modification comprises a 2'-MOE sugar modification.

Antisense compounds having a gapmer motif are considered "chimeric" antisense compounds or "chimeras," which contain two or more chemically distinct regions, each made up of at least one monomer unit, i.e., a nucleotide in the case of an oligonucleotide compound. These oligonucleotides typically contain at least one region modified so as to confer increased resistance to nuclease degradation, increased cellular uptake, increased binding affinity for the target nucleic acid, and/or increased inhibitory activity. It is not necessary for all positions in a given compound to be uniformly modified, and in fact more than one of the aforementioned modifications may be incorporated in a single compound or even at a single nucleoside within an oligonucleotide.

An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

In the case of an antisense oligonucleotide having a gapmer motif, the gap segment generally serves as the substrate for endonuclease cleavage, while the wing segments comprise modified nucleosides. In a preferred embodiment, the regions of a gapmer are differentiated by the types of sugar moieties comprising each distinct region. The types of sugar moieties that are used to differentiate the regions of a gapmer may include β-D-ribonucleosides, β-D-deoxyribonucleosides, 2'-modified nucleosides (such 2'-modified nucleosides may include 2'-MOE), and bicyclic sugar modified nucleosides.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

In another embodiment of the invention, the compound comprises the modified oligonucleotide consists of 20 linked nucleosides.

In a preferred embodiment of the invention, the compound comprises the nucleobase sequence is the sequence set forth in SEQ ID NOs: 39, 40, 45, 52 and 166.

In one embodiment of the invention the composition comprises a modified oligonucleotide comprising linked nucleosides, the nucleobase sequence of which is a sequence set forth in one of SEQ ID NOs: 28, 30, 39, 40, 43, 44, 45, 50, 51, 52, 56, 78, 125 and 166 or a salt thereof, and a pharmaceutically acceptable carrier or diluent. Examples of pharmaceutically acceptable salts are well known to those skilled in the art.

In one embodiment of the invention, the antisense compound is complementary within a range of nucleotides on the CTGF sequence. In certain embodiments the antisense compound is complimentary within the range of nucleotides 718-751, 1388-1423, 1457-1689, 2040-2069, 2120-2147, or 2267-2301 of SEQ ID NO: 9. In a certain embodiment the antisense compound is complimentary within the range of nucleotides 2728-2797 of SEQ ID NO: 10. Compounds targeted to these ranges demonstrate at least 50% inhibition (i.e. SEQ ID NOs: 15, 29, 31, 42, 46-49, 53, 72, 81, 82, 152-154, 164, and 165). Certain target sites listed in Table 1 also demonstrate at least 50% inhibition (i.e. SEQ ID NOs: 12, 20, 33, 34, 76, 107, 129, 132, 134, 136, and 146). In certain embodiments the antisense compound is complementary within the range of nucleotides 553-611, 1394-1423, 1469-1508, 1559-1605, 1659-1689 or 2100-2129 of SEQ ID NO: 9 and 2623-2647 of SEQ ID NO: 10. Compounds targeted therein demonstrate at least 60% inhibition (i.e. SEQ ID NOs: 27, 28, 38, 39, 40, 43, 44, 45, 50, 51, 52, 54, 55, 56, 77, 78, 79, 138 and 139). Certain additional target sites listed in Table 1 also demonstrate at least 60% inhibition (i.e. SEQ ID NOs: 24, 30, 61, 63, 67, 69, 73, 86, 125, 128, and 161). In certain embodiments the antisense compound is complementary within the range of nucleotides 1399-1423. Compounds targeted therein demonstrate at least 70% inhibition (i.e. SEQ ID NOs: and 40). Certain target sites listed in Table 1 also demonstrate at least 70% inhibition (i.e. SEQ ID NOs: 28, 30, 44, 45, 51, 56, 78, 128, and 138). One target site listed in Table 1 also demonstrates at least 80% inhibition (i.e. SEQ ID NO: 44). In certain embodiments, the percent inhibition is achieved when the antisense compound is delivered to HuVec cells at a concentration of 50 nm. Refer to Example 8, provided herein below, for more details.

In an embodiment of the composition, the modified oligonucleotide is a single-stranded or double stranded oligonucleotide. In another embodiment of the invention, comprising a modified oligonucleotide, wherein the modified oligonucleotide consists of 20 linked nucleosides In another embodiment of the invention, provides a method for inhibiting expression of connective tissue growth factor in a cell or a tissue which comprises contacting the cell or tissue with the compound of interest under conditions such that expression of connective tissue growth factor is inhibited.

Compositions and Methods for Formulating Pharmaceutical Compositions

Antisense oligonucleotides may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a nucleic acid and a pharmaceutically acceptable diluent. In one embodiment, the pharmaceutically acceptable diluent is PBS. In another embodiment, the pharmaceutically acceptable diluent is pharmaceutical grade saline or pharmaceutical grade PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

In certain embodiment of the invention, a pharmaceutically acceptable carrier or diluent is an ingredient in a composition that lacks pharmacological activity, but is pharmaceutically necessary or desirable as a solvent, suspending agent or any other pharmaceutically inert vehicle for delivering one or more nucleic acids to a human or non-human animal. Pharmaceutical carriers are well known to those skilled in the art.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

In one embodiment of the invention, the composition comprises a modified oligonucleotide comprises a single-stranded or a double-stranded oligonucleotide, and wherein the modified oligonucleotide consists of 20 linked nucleosides.

In another embodiment of the invention involves a method for inhibiting expression of connective tissue growth factor in a cell or a tissue which comprises contacting the cell or tissue with any one of the above-mentioned compounds under conditions such that expression of connective tissue growth factor is inhibited.

In certain embodiment of the invention involves a method of treating an animal having a disease or condition associated with expression of connective tissue growth factor which comprises administering to the animal an amount of the compound described hereinabove effective to inhibit expression of connective tissue growth factor so as to thereby treat the animal.

In the practice of the method of this invention, an animal includes a human as well as a non-human animal, preferably human.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethyl-ethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(iso-hexylcynaoacrylate), DEAE-methacrylate, DEAE-hexylacrylate, DEAE-acrylamide, DEAE-albumin and DEAE-dextran, polymethyl-acrylate, polyhexylacrylate, poly(D,L-lactic acid), poly(DL-lactic-co-glycolic acid (PLGA), alginate, and polyethylene-glycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethyl-cellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, non-swelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}$ 15G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxy-cholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mito-xantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially. In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Certain Indications

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In certain embodiment of the invention provides a method of treating a disease or condition associated with expression of CTGF, wherein the disease is a hyperproliferative disorder which includes cancer, wherein the cancer is breast, prostate, renal, pancreatic, head and neck, gastric, and multiple myeloma cancer (See Pickles M and Leask A, J Cell Commun Signal. 2007 September; 1(2):85-90. Epub 2007 Jul. 17; Mullis T. C., Tang X., Chong K. T., J Clin Pathol. 2008 May; 61(5):606-10; Liu L. Y., et al. World J. Gastroenterol. 2008 Apr. 7; 14(13):2110-4; Chintalapudi M. R., et al., Carcinogenesis. 2008 April; 29(4):696-703. Epub 2008 Jan. 22; Munemasa S., et al. Br J. Haematol. 2007 October; 139(1):41-50; Shimo T., et al. J Bone Miner Res. 2006 July; 21(7):1045-59; and Yang F., et al. Cancer Res. 2005 Oct. 1; 65(19):8887-95.)

In one embodiment of the invention the method comprises treating a disease or condition, wherein the disease or disorder is a fibrotic disease. In one embodiment of the method of the invention, the fibrotic disease is hypertrophic scarring, keloids, skin scarring, liver fibrosis, pulmonary fibrosis, renal fibrosis, cardiac fibrosis, or restenosis.

In another embodiment of the invention, the method further comprises treating the above-mentioned disease or condition, wherein the disease or disorder is joint fibrosis (including frozen shoulder syndrome, tendon and peripheral nerve damage), spinal cord damage, coronary bypass, abdominal and peritoneal adhesions (including endometriosis, uterine leiomyomata and fibroids), radial keratotomy and photorefractive keratectomy, retinal reattachment surgery, device mediated fibrosis (in for example diabetes), tendon adhesions, Dupuytren contracture, or scleroderma.

In another embodiment of the invention also provides a method for reducing hypertropic scarring resulting from dermal wound healing in a subject in need thereof which comprises administering to the subject an amount of compound of an antisense oligonucleotide effective to inhibit expression of connective tissue growth factor (CTGF) in the subject so as to thereby reduce scarring from wound healing in the subject. The say subject may include a human or a non-human animal.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In another embodiment of this invention, the method further comprises reducing hypertropic scarring resulting from dermal wound healing, wherein wound healing is healing at a wound selected from the group consisting of skin breakage, surgical incisions and burns.

In certain embodiments, the invention provides methods of treating an individual comprising administering one or more pharmaceutical compositions of the present invention. In certain embodiments, the individual has one of the above mentioned disorders. In certain embodiments, the individual is at risk for one of the above mentioned disorders. In certain embodiments, the individual has been identified as in need of therapy. In certain embodiments the invention provides methods for prophylactically reducing CTGF expression in an individual.

Certain embodiments include treating an individual in need thereof by administering to an individual a therapeutically effective amount of an antisense compound targeted to a CTGF nucleic acid.

In one embodiment, administration of a therapeutically effective amount of an antisense compound targeted to a CTGF nucleic acid is accompanied by monitoring of CTGF levels in the serum of an individual, to determine an individual's response to administration of the antisense compound. An individual's response to administration of the antisense compound is used by a physician to determine the amount and duration of therapeutic intervention.

In one embodiment, administration of an antisense compound targeted to a CTGF nucleic acid results in reduction of CTGF expression by at least 15, 20, 25, 30, 35, 40, 45, 50, 55, 60, 65, 70, 75, 80, 85, 90, 95 or 99%, or a range defined by any two of these values. In one embodiment, administration of an antisense compound targeted to a CTGF nucleic acid results in a change in a measure of CTGF as measured by a standard test, for example, but not limited to, CTGF. In some embodiments, administration of a CTGF antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a CTGF antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments pharmaceutical composition comprising an antisense compound targeted to CTGF is used for the preparation of a medicament for treating a patient suffering or susceptible to any one of the above-mentioned disorders.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include a second therapeutic agent. In certain such embodiments, pharmaceutical agents that may be co-administered with a pharmaceutical composition of the present invention include, but are not limited to second therapeutic agent. In certain such embodiments, the second therapeutic agent is administered prior to administration of a pharmaceutical composition of the present invention. In certain such embodiments, the second therapeutic agent is administered following administration of a pharmaceutical composition of the present invention. In certain such embodiments the second therapeutic agent is administered at the same time as a pharmaceutical composition of the present invention. In certain such embodiments the dose of a co-administered second therapeutic agent is the same as the dose that would be administered if the second therapeutic agent was administered alone. In certain such embodiments the dose of a co-administered second therapeutic agent is lower than the dose that would be administered if the second therapeutic agent was administered alone. In certain such embodiments the dose of a co-administered second therapeutic agent is greater than the dose that would be administered if the second therapeutic agent was administered alone.

In certain embodiments, the co-administration of a second compound enhances the therapeutic effect of a first compound, such that co-administration of the compounds results in an therapeutic effect that is greater than the effect of administering the first compound alone, a synergistic effect. In other embodiments, the co-administration results in therapeutic effects that are additive of the effects of the compounds when administered alone. In other embodiments, the co-administration results in therapeutic effects that are supra-additive of the effects of the compounds when administered alone. In some embodiments, the first compound is an antisense compound. In some embodiments, the second compound is an antisense compound.

This invention is illustrated in the Experimental Details Section which follows. This section is set forth to aid in an understanding of the invention but is not intended to, and should not be construed to limit in any way the invention as set forth in the claims which follow thereafter.

EXAMPLES

Example 1

Cell Culture and Antisense Compounds Treatment

The effects of antisense compounds on the level, activity or expression of CTGF nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

Example 2

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 µg/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 µg/mL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM.

Example 3

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Example 4

Analysis of Inhibition of Target Levels or Expression

Inhibition of levels or expression of a CTGF nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Example 5

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invetrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a CTGF nucleic acid. Methods for designing real-time PCR probes and primers are well known in the art, and may include the use of software such as PRIMER EXPRESS® Software (Applied Biosystems, Foster City, Calif.).

Example 6

Analysis of Protein Levels

Antisense inhibition of CTGF nucleic acids can be assessed by measuring CTGF protein levels. Protein levels of CTGF can be evaluated or quantitated in a variety of ways well known in the art, such as immunoprecipitation, Western blot analysis (immunoblotting) as described in Example 9 below, enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat CTGF are commercially available.

Example 7

In Vivo Testing of Antisense Compounds

Antisense compounds, for example, antisense oligonucleotides, are tested in animals to assess their ability to inhibit expression of CTGF and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in CTGF nucleic acid expression are measured. Changes in CTGF protein levels are also measured using the methods described hereinabove in Example 6.

Example 8

Selection of Lead Human Connective Tissue Growth Factors (CTGF) Antisense Oligonucleotides Candidate Introduction In accordance with the present invention, a series of oligonucleotides were designed to target different regions of the human connective tissue growth factor RNA, using published sequences (GenBank accession number NM 001901.2, incorporated herein as SEQ ID NO: 9, and GenBank accession number NT_025741.14, incorporated herein as SEQ ID NO: 10).

This study analyzes available sequence space and modified antisense oligonucleotides targeting both exonic and intronic space of CTGF. Approximately 150 novel sequences per target were synthesized and evaluated for activity against CTGF in cell-culture. The oligonucleotides are shown in Table 1. All compounds in Table 1 are chimeric oligonucleotides ("gapmers") 20 nucleotides in length, composed of a central "gap" region consisting of either ten 2'-deoxynucleotides, which is flanked on both sides (5' and 3' directions) by five-nucleotides "wings" or 13 2'-deoxynucleotides, which is flanked on both sides (5' and 3' directions) by two- and five-nucleotides "wings," respectively. The wings are composed of 2'-methoxyethyl (2'-MOE) nucleotides. The internucleoside (backbone) linkages are phosphorothioate (P=S) throughout the oligonucleotide. All cystidine residuals are 5-methycytidines. The compounds were analyzed for their effect on human connective tissue growth factor mRNA levels by quantitative real-time PCR as described in other examples herein. Data are averages from two experiments. If present, "N.D." indicates "no data".

TABLE 1

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 124173 | CDS | 9 | 380 | CCAGCTGCTTGGCGCAGACG | 35 | 11 |
| 124189 | CDS | 9 | 1003 | GCCAGAAAGCTCAAACTTGA | 57 | 12 |
| 124212 | 3'-UTR | 9 | 1783 | CCACAAGCTGTCCAGTCTAA | 47 | 13 |
| 124235 | 3'-UTR | 9 | 2267 | GGTCACACTCTCAACAAATA | 47 | 14 |
| 124238 | 3'-UTR | 9 | 2282 | AAACATGTAACTTTTGGTCA | 53 | 15 |
| 412271 | 5'-UTR | 9 | 4 | GGGAAGAGTTGTTGTGTGAG | 0 | 16 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412272 | 5'-UTR | 9 | 38 | AGGGTGGAGTCGCACTGGCT | 46 | 17 |
| 412273 | CDS | 9 | 228 | ACGAAGGCGACGCGGACGGG | 35 | 18 |
| 412274 | CDS | 9 | 265 | GCCGACGGCCGGCCGGCTGC | 40 | 19 |
| 412275 | CDS | 9 | 475 | GGTGCACACGCCGATCTTGC | 52 | 20 |
| 412276 | CDS | 9 | 483 | TCTTTGGCGGTGCACACGCC | 0 | 21 |
| 412277 | CDS | 9 | 489 | GCACCATCTTTGGCGGTGCA | 0 | 22 |
| 412278 | CDS | 9 | 496 | GCAGGGAGCACCATCTTTGG | 16 | 23 |
| 412279 | CDS | 9 | 501 | AAGATGCAGGGAGCACCATC | 63 | 24 |
| 412280 | CDS | 9 | 507 | CCACCGAAGATGCAGGGAGC | 0 | 25 |
| 412281 | CDS | 9 | 512 | CCGTACCACCGAAGATGCAG | 47 | 26 |
| 412282 | CDS | 9 | 553 | GTACTTGCAGCTGCTCTGGA | 68 | 27 |
| 412283 | CDS | 9 | 592 | GGGCATGCAGCCCACCGCCC | 72 | 28 |
| 412284 | CDS | 9 | 718 | AGGCCCAACCACGGTTTGGT | 59 | 29 |
| 412285 | CDS | 9 | 723 | AGGGCAGGCCCAACCACGGT | 79 | 30 |
| 412286 | CDS | 9 | 732 | TAAGCCGCGAGGGCAGGCCC | 55 | 31 |
| 412287 | CDS | 9 | 829 | CCCACAGGTCTTGGAACAGG | 30 | 32 |
| 412288 | CDS | 9 | 839 | AGATGCCCATCCCACAGGTC | 55 | 33 |
| 412289 | 3'-UTR | 9 | 1273 | CCAGTCTAATGAGTTAATGT | 56 | 34 |
| 412290 | 3'-UTR | 9 | 1281 | TTCAAGTTCCAGTCTAATGA | 10 | 35 |
| 412291 | 3'-UTR | 9 | 1361 | TTTTCCCCCAGTTAGAAAAA | 38 | 36 |
| 412292 | 3'-UTR | 9 | 1388 | CACAATGTTTTGAATTGGGT | 50 | 37 |
| 412293 | 3'-UTR | 9 | 1394 | ACATGGCACAATGTTTTGAA | 67 | 38 |
| 412294 | 3'-UTR | 9 | 1399 | GTTTGACATGGCACAATGTT | 73 | 39 |
| 412295 | 3'-UTR | 9 | 1404 | TATTTGTTTGACATGGCACA | 74 | 40 |
| 412296 | 3'-UTR | 9 | 1412 | TGATAGACTATTTGTTTGAC | 35 | 41 |
| 412297 | 3'-UTR | 9 | 1457 | GTTCCACTGTCAAGTCTTAA | 55 | 42 |
| 412298 | 3'-UTR | 9 | 1469 | TGTACTAATGTAGTTCCACT | 69 | 43 |
| 412299 | 3'-UTR | 9 | 1482 | CATTCTGGTGCTGTGTACTA | 86 | 44 |
| 412300 | 3'-UTR | 9 | 1489 | TAATATACATTCTGGTGCTG | 76 | 45 |
| 412301 | 3'-UTR | 9 | 1495 | ACACCTTAATATACATTCTG | 54 | 46 |
| 412302 | 3'-UTR | 9 | 1502 | TAAAGCCACACCTTAATATA | 54 | 47 |
| 412303 | 3'-UTR | 9 | 1520 | GTACCCTCCCACTGCTCCTA | 53 | 48 |
| 412304 | 3'-UTR | 9 | 1554 | AAGATGCTATCTGATGATAC | 52 | 49 |
| 412305 | 3'-UTR | 9 | 1559 | CGTATAAGATGCTATCTGAT | 69 | 50 |
| 412306 | 3'-UTR | 9 | 1577 | AATAGCAGGCATATTACTCG | 74 | 51 |
| 412307 | 3'-UTR | 9 | 1586 | TACACTTCAAATAGCAGGCA | 69 | 52 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412308 | 3'-UTR | 9 | 1591 | TCAATTACACTTCAAATAGC | 50 | 53 |
| 412309 | 3'-UTR | 9 | 1659 | GGAGAATGCACATCCTAGCT | 66 | 54 |
| 412310 | 3'-UTR | 9 | 1665 | ATGGCTGGAGAATGCACATC | 60 | 55 |
| 412311 | 3'-UTR | 9 | 1670 | TCTTGATGGCTGGAGAATGC | 71 | 56 |
| 412312 | 3'-UTR | 9 | 1729 | GAATCAGAATGTCAGAGCTG | 37 | 57 |
| 412313 | 3'-UTR | 9 | 1946 | CATTGAAATATCAAAGCATT | 0 | 58 |
| 412314 | 3'-UTR | 9 | 1952 | GGCTAACATTGAAATATCAA | 25 | 59 |
| 412315 | 3'-UTR | 9 | 1958 | AATTGAGGCTAACATTGAAA | 1 | 60 |
| 412316 | 3'-UTR | 9 | 1965 | GTTCAGAAATTGAGGCTAAC | 65 | 61 |
| 412317 | 3'-UTR | 9 | 1971 | TATGGTGTTCAGAAATTGAG | 13 | 62 |
| 412318 | 3'-UTR | 9 | 1976 | CTACCTATGGTGTTCAGAAA | 61 | 63 |
| 412319 | 3'-UTR | 9 | 1982 | TACATTCTACCTATGGTGTT | 38 | 64 |
| 412320 | 3'-UTR | 9 | 1991 | GACAAGCTTTACATTCTACC | 24 | 65 |
| 412321 | 3'-UTR | 9 | 1996 | GATCAGACAAGCTTTACATT | 37 | 66 |
| 412322 | 3'-UTR | 9 | 2007 | ATGCTTTGAACGATCAGACA | 64 | 67 |
| 412323 | 3'-UTR | 9 | 2012 | ATTTCATGCTTTGAACGATC | 44 | 68 |
| 412324 | 3'-UTR | 9 | 2018 | GTATCCATTTCATGCTTTGA | 60 | 69 |
| 412325 | 3'-UTR | 9 | 2026 | CCATATAAGTATCCATTTCA | 48 | 70 |
| 412326 | 3'-UTR | 9 | 2032 | GAATTTCCATATAAGTATCC | 28 | 71 |
| 412327 | 3'-UTR | 9 | 2040 | TCTGAGCAGAATTTCCATAT | 58 | 72 |
| 412328 | 3'-UTR | 9 | 2050 | TGTCATTCTATCTGAGCAGA | 61 | 73 |
| 412329 | 3'-UTR | 9 | 2060 | TTTGACGGACTGTCATTCTA | 47 | 74 |
| 412330 | 3'-UTR | 9 | 2070 | AACAATCTGTTTTGACGGAC | 48 | 75 |
| 412331 | 3'-UTR | 9 | 2088 | TGATGCCTCCCCTTTGCAAA | 53 | 76 |
| 412332 | 3'-UTR | 9 | 2100 | TGCCAAGGACACTGATGCCT | 68 | 77 |
| 412333 | 3'-UTR | 9 | 2105 | CAGCCTGCCAAGGACACTGA | 75 | 78 |
| 412334 | 3'-UTR | 9 | 2110 | GAAATCAGCCTGCCAAGGAC | 60 | 79 |
| 412335 | 3'-UTR | 9 | 2115 | ACCTAGAAATCAGCCTGCCA | 46 | 80 |
| 412336 | 3'-UTR | 9 | 2120 | TTCCTACCTAGAAATCAGCC | 51 | 81 |
| 412337 | 3'-UTR | 9 | 2128 | TACCACATTTCCTACCTAGA | 59 | 82 |
| 412338 | 3'-UTR | 9 | 2134 | TGAGGCTACCACATTTCCTA | 0 | 83 |
| 412339 | 3'-UTR | 9 | 2140 | TAAAAGTGAGGCTACCACAT | 48 | 84 |
| 412340 | 3'-UTR | 9 | 2213 | CAAATGCTTCCAGGTGAAAA | 49 | 85 |
| 412341 | 3'-UTR | 9 | 2219 | TAGAAACAAATGCTTCCAGG | 66 | 86 |
| 412342 | 3'-UTR | 9 | 2230 | TCATATCAAAGTAGAAACAA | 12 | 87 |
| 412343 | 3'-UTR | 9 | 2242 | TCCGAAAAACAGTCATATCA | 24 | 88 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412368 | Intron 1 | 10 | 1308 | ACCCGGCTGCAGAGGGCGAG | 0 | 89 |
| 412369 | Intron 1 | 10 | 1313 | CGCTTACCCGGCTGCAGAGG | 0 | 90 |
| 412370 | Intron 1 | 10 | 1410 | GACAGGGCGGTCAGCGGCGC | 0 | 91 |
| 412371 | Intron 2 | 10 | 1730 | AGTCCGAGCGGTTTCTTTTT | 0 | 92 |
| 412372 | Intron 2 | 10 | 1735 | AACTCAGTCCGAGCGGTTTC | 19 | 93 |
| 412373 | Intron 2 | 10 | 1740 | AAAGAAACTCAGTCCGAGCG | 10 | 94 |
| 412374 | Intron 2 | 10 | 1745 | TGGAGAAAGAAACTCAGTCC | 45 | 95 |
| 412375 | Intron 2 | 10 | 1750 | GCAGCTGGAGAAAGAAACTC | 14 | 96 |
| 412376 | Intron 2 | 10 | 1755 | TGGCAGCAGCTGGAGAAAGA | 46 | 97 |
| 412377 | Intron 2 | 10 | 1887 | AGGGAGCACCATCTTTGGCT | 20 | 98 |
| 412378 | Intron 3 | 10 | 2125 | TCACCCGCGAGGGCAGGCCC | 33 | 99 |
| 412379 | Intron 3 | 10 | 2137 | GGAAGACTCGACTCACCCGC | 0 | 100 |
| 412380 | Intron 3 | 10 | 2142 | TTAGAGGAAGACTCGACTCA | 0 | 101 |
| 412381 | Intron 3 | 10 | 2150 | ACCCTGACTTAGAGGAAGAC | 47 | 102 |
| 412382 | Intron 3 | 10 | 2155 | TCACGACCCTGACTTAGAGG | 31 | 103 |
| 412383 | Intron 3 | 10 | 2160 | GAGAATCACGACCCTGACTT | 2 | 104 |
| 412384 | Intron 3 | 10 | 2165 | TGGGAGAGAATCACGACCCT | 31 | 105 |
| 412385 | Intron 3 | 10 | 2170 | CTCCCTGGGAGAGAATCACG | 0 | 106 |
| 412386 | Intron 3 | 10 | 2191 | GGTCGGCACAGTTAGGACTC | 53 | 107 |
| 412387 | Intron 3 | 10 | 2196 | CGTTCGGTCGGCACAGTTAG | 30 | 108 |
| 412388 | Intron 3 | 10 | 2216 | CCTGGATAAGGTATTTCCCC | 0 | 109 |
| 412389 | Intron 3 | 10 | 2235 | ACAAACACCATGTAAAACGC | 11 | 110 |
| 412390 | Intron 3 | 10 | 2241 | GAGCACACAAACACCATGTA | 0 | 111 |
| 412391 | Intron 3 | 10 | 2251 | TGCGAGAGCAGAGCACACAA | 0 | 112 |
| 412392 | Intron 3 | 10 | 2256 | TAAGCTGCGAGAGCAGAGCA | 2 | 113 |
| 412393 | Intron 3 | 10 | 2261 | GTCGGTAAGCTGCGAGAGCA | 23 | 114 |
| 412394 | Intron 3 | 10 | 2266 | TTCCAGTCGGTAAGCTGCGA | 15 | 115 |
| 412395 | Intron 4 | 10 | 2472 | ACATGTACCTTAATGTTCTC | 0 | 116 |
| 412396 | Intron 4 | 10 | 2477 | GCAGAACATGTACCTTAATG | 0 | 117 |
| 412397 | Intron 4 | 10 | 2482 | TAGGAGCAGAACATGTACCT | 9 | 118 |
| 412398 | Intron 4 | 10 | 2487 | GTTAATAGGAGCAGAACATG | 19 | 119 |
| 412399 | Intron 4 | 10 | 2496 | TGAAAATAGTTAATAGGAG | 0 | 120 |
| 412400 | Intron 4 | 10 | 2511 | CCACTGTTTTTCCTGTGAAA | 10 | 121 |
| 412401 | Intron 4 | 10 | 2525 | AAGTTGGGTCCTATCCACTG | 28 | 122 |
| 412402 | Intron 4 | 10 | 2530 | GCCCAAGTTGGGTCCTATC | 20 | 123 |
| 412403 | Intron 4 | 10 | 2535 | CAAGAGCCCAAGTTGGGTC | 0 | 124 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412404 | Intron 4 | 10 | 2540 | CGTGGCAAGAGCCCTAAGTT | 64 | 125 |
| 412405 | Intron 4 | 10 | 2558 | CGGGCTTATACTAACAAGCG | 6 | 126 |
| 412406 | Intron 4 | 10 | 2563 | GATAACGGGCTTATACTAAC | 33 | 127 |
| 412407 | Intron 4 | 10 | 2568 | TTGGAGATAACGGGCTTATA | 73 | 128 |
| 412408 | Intron 4 | 10 | 2573 | TAGTTTTGGAGATAACGGGC | 51 | 129 |
| 412409 | Intron 4 | 10 | 2578 | TTAGATAGTTTTGGAGATAA | 24 | 130 |
| 412410 | Intron 4 | 10 | 2584 | CAATGGTTAGATAGTTTTGG | 36 | 131 |
| 412411 | Intron 4 | 10 | 2589 | CAGCTCAATGGTTAGATAGT | 53 | 132 |
| 412412 | Intron 4 | 10 | 2594 | CAAAACAGCTCAATGGTTAG | 34 | 133 |
| 412413 | Intron 4 | 10 | 2599 | TCCAGCAAAACAGCTCAATG | 59 | 134 |
| 412414 | Intron 4 | 10 | 2604 | CTCATTCCAGCAAAACAGCT | 42 | 135 |
| 412415 | Intron 4 | 10 | 2609 | AAGCTCTCATTCCAGCAAAA | 57 | 136 |
| 412416 | Intron 4 | 10 | 2614 | TACACAAGCTCTCATTCCAG | 44 | 137 |
| 412417 | Intron 4 | 10 | 2623 | GGTTGCTATTACACAAGCTC | 72 | 138 |
| 412418 | Intron 4 | 10 | 2628 | CTGGTGGTTGCTATTACACA | 61 | 139 |
| 412419 | Intron 4 | 10 | 2633 | GAAAACTGGTGGTTGCTATT | 29 | 140 |
| 412420 | Intron 4 | 10 | 2638 | TAGTGGAAAACTGGTGGTTG | 5 | 141 |
| 412421 | Intron 4 | 10 | 2663 | TTAACTAACCCTGTGGAAGA | 15 | 142 |
| 412422 | Intron 4 | 10 | 2672 | TGTCTTGAATTAACTAACCC | 4 | 143 |
| 412423 | Intron 4 | 10 | 2677 | TGGAATGTCTTGAATTAACT | 0 | 144 |
| 412424 | Intron 4 | 10 | 2691 | GCCAGAGCCTCTCTTGGAAT | 36 | 145 |
| 412425 | Intron 4 | 10 | 2698 | AAAAATAGCCAGAGCCTCTC | 59 | 146 |
| 412426 | Intron 4 | 10 | 2703 | TGTCCAAAAATAGCCAGAGC | 28 | 147 |
| 412427 | Intron 4 | 10 | 2708 | TGCTATGTCCAAAAATAGCC | 15 | 148 |
| 412428 | Intron 4 | 10 | 2713 | TCATTTGCTATGTCCAAAAA | 28 | 149 |
| 412429 | Intron 4 | 10 | 2718 | GAGTCTCATTTGCTATGTCC | 20 | 150 |
| 412430 | Intron 4 | 10 | 2723 | AGTTTGAGTCTCATTTGCTA | 30 | 151 |
| 412431 | Intron 4 | 10 | 2728 | GAGGAAGTTTGAGTCTCATT | 55 | 152 |
| 412432 | Intron 4 | 10 | 2763 | CTTCTGTTGTCTGACTTCTG | 55 | 153 |
| 412433 | Intron 4 | 10 | 2778 | CCTCTGTGTTTAGTCTTCT | 56 | 154 |
| 412434 | Intron 4 | 10 | 2788 | TTTCTTCAACCCTCTGTGTT | 15 | 155 |
| 412435 | Intron 4 | 10 | 2796 | GGAGTGGCTTTCTTCAACCC | 43 | 156 |
| 412436 | Intron 4 | 10 | 2849 | AGGAAGACAAGGGAAAAGAG | 20 | 157 |
| 412437 | Intron 4 | 10 | 2854 | TTCTAAGGAAGACAAGGGAA | 0 | 158 |
| 412438 | Intron 4 | 10 | 2859 | TGCCCTTCTAAGGAAGACAA | 31 | 159 |
| 412439 | Intron 2 | 10 | 1791 | GGATGCGAGTTGGGATCTGG | 0 | 160 |

TABLE 1-continued

Inhibition of human connective tissue growth factor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO. |
|---|---|---|---|---|---|---|
| 412440 | CDS | 9 | 380 | CCAGCTGCTTGGCGCAGACG | 64 | 161 |
| 412441 | CDS | 9 | 1003 | GCCAGAAAGCTCAAACTTGA | 37 | 162 |
| 412442 | 3'-UTR | 9 | 1783 | CCACAAGCTGTCCAGTCTAA | 32 | 163 |
| 412443 | 3'-UTR | 9 | 2267 | GGTCACACTCTCAACAAATA | 59 | 164 |
| 412444 | 3'-UTR | 9 | 2282 | AAACATGTAACTTTTGGTCA | 55 | 165 |
| 418899 | 3'-UTR | 9 | 1391 | TGACATGGCACAATGTTTTG | ND* | 166 |

*ND-i.e. not determined in the experiment but was highly active in another assay.

As shown in Table 1, SEQ ID NOs 11-15, 17-20, 24, 26-34, 36-57, 59, 61, 63-82, 84-86, 88, 95, 97, 99, 102, 103, 105, 107, 108, 122, 125, 127-140, 145, 146, 149, 151-154, 156, 159, 161-165 demonstrated at least 24% inhibition of human connective tissue growth factor expression in this assay and are therefore preferred. The target sites to which these preferred sequences are complementary are herein referred to as "active sites" and are therefore preferred sites for targeting by compounds of the present invention.

The antisense compound is complementary within a range of nucleotides on the CTGF sequence, i.e. within the range of nucleotides 718-751, 1388-1423, 1457-1689, 2040-2069, 2120-2147, or 2267-2301 of SEQ ID NO: 9. In a certain embodiment the antisense compound is complimentary within the range of nucleotides 2728-2797 of SEQ ID NO: 10. Compounds targeted to these ranges demonstrate at least 50% inhibition (i.e. SEQ ID NOs: 15, 29, 31, 42, 46-49, 53, 72, 81, 82, 152-154, 164, and 165). Certain target sites listed in Table 1 also demonstrate at least 50% inhibition (i.e. SEQ ID NOs: 12, 20, 33, 34, 76, 107, 129, 132, 134, 136, and 146).

In certain embodiments the antisense compound is complementary within the range of nucleotides 553-611, 1394-1423, 1469-1508, 1559-1605, 1659-1689 or 2100-2129. Compounds targeted therein demonstrate at least 60% inhibition (i.e. SEQ ID NOs: 27, 38, 43, 50, 52, 54, 55, 77, 79, and 86). Certain target sites listed in Table 1 also demonstrate at least 60% inhibition (i.e. SEQ ID NOs: 24, 61, 63, 67, 69, 73, 125, 139 and 161).

The antisense compound is also complementary within the range of nucleotides 1399-1423. Compounds targeted therein demonstrate at least 70% inhibition (i.e. SEQ ID NOs: 39 and 40). Certain target sites listed in Table 1 also demonstrate at least 70% inhibition (i.e. SEQ ID NOs: 28, 30, 45, 51, 56, 78, 128, and 138). One target site listed in Table 1 also demonstrates at least 80% inhibition (i.e. SEQ ID NO: 44). In certain embodiments, the percent inhibition is achieved when the antisense compound is delivered to HuVec cells at a concentration of 50 nm.

Multiple leads with apparent activity greater than the historical ASO lead sequence, SEQ ID No. 15 (ISIS 124238), were identified in both exonic and intronic sequences.

Dose response studies on nine highly active sequences (SEQ ID Nos: 28, 30, 39, 40, 45, 52, 56, 78, 125) were completed (see FIG. 8). SEQ NO. 13 and 15 (ISIS 124212 and 124238) are the previously designated oligonucleotides and SEQ ID No: 167 (ISIS 141923, sequence CCTTCCCTGA AGGTTCCTCC) is the negative control.

Materials and Methods

Oligonucleotides were screened and confirmed at a concentration 50 nM in human umbilical vein endothelial cells (HuVEC) using Lipofectin mediated transfection. HuVEC cells from Cascade Biologics (Portland, Oreg.) maintained in Medium 200 supplemented with Low Serum Growth Supplement (from Cascade Biologics) were plated into 96-well plates at 5,000 cells per well and incubated overnight at 37° C. in the presence of 5% $CO_2$. The following day the medium was aspirated and replaced with prewarmed Opti-MEM I (Invitrogen) containing Oligo-Lipofectamine 2000 (Invitrogen) mixture (3 mg of Lipofectamine 2000 per 1 ml of Opti-MEM I medium). After 4 hours, the transfection mixture was exchanged for fresh Medium 200 supplemented with Low Serum Growth Supplement and incubated at 37° C. in the presence of 5% $CO_2$. After 16-24 hours, at approximately 80% confluence, the cells were washed with phosphate buffer saline (PBS) and lysed for RNA purification with the Qiagen RNeasy Kit. CTGF message was measured by quantitative real time polymerase chain reaction (RT-PCR) (Primer/Probe sets shown below) and the results were normalized to total RNA.

Statistical Analysis

Each sample was analyzed in duplicate, and vertical bars represent the spread between the two measurements.

Results and Discussion

Of the approximately 150 novel sequences per target synthesized and evaluated for activity against CTGF in cell-culture, the new CTGF oligonucleotides (SEQ ID NOs: 28, 30, 39, 40, 45, 52, 56, 78, 125, and 166) show excellent inhibition of human CTGF mRNA expression. The highly active oligonucleotides identified are provided in FIGS. 7A and 7B.

A number of new intronic (FIGS. 4, 5 and 6) and exonic (FIGS. 1, 2 and 3) oligonucleotides surprisingly are significantly more active than the historical previously screened compounds, including ISIS 124238.

The efficiency of antisense targeting exons is generally higher than those targeting introns. (FIG. 7A). A listing of these exonic nucleotide sequences are provided in FIG. 7B.

The top 10 most active antisense oligonucleotides were confirmed in dose response experiments in HuVEC cells using the method described above.

Example 9

Western Blot Analysis of Connective Tissue Growth Factor Protein Levels

Western blot analysis (immunoblot analysis) is carried out using standard methods. Cells are harvested 16-20 hours after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to connective tissue growth factor is used, with a radiolabelled or fluorescently labeled secondary antibody directed against the primary antibody species. Bands are visualized using a PHOSPHORIMAGER™ (Molecular Dynamics, Sunnyvale Calif.).

Example 10

CTGF Antisense Oligonucleotide Pilot Mouse Toxicology Study

Study Objective

The purpose of this pilot toxicology study was to evaluate three oligonucleotides targeting human CTGF for potential toxicity in normal male BALB/c mice. The oligonucleotides tested were ISIS sequences 412294 (SEQ ID NO: 39), 412295 (SEQ ID NO: 40), and 418899 (SEQ ID NO: 166).

Methods

Male BALB/c mice (approximately 8 weeks old) weighing approximately 25 grams were fed a normal lab chow diet throughout the study. The mice were dosed subcutaneously (SQ) twice per week with 25 or 50 mg/kg antisense oligonucleotides for 4 weeks (n=6). The following endpoints were measured:

Weekly Body Weights;
Blood Plasma Chemistries at 4 weeks;
Organ weight, Body weight at necropsy; and
H&E stain of Liver and Kidney.

Results

Figure 9A:
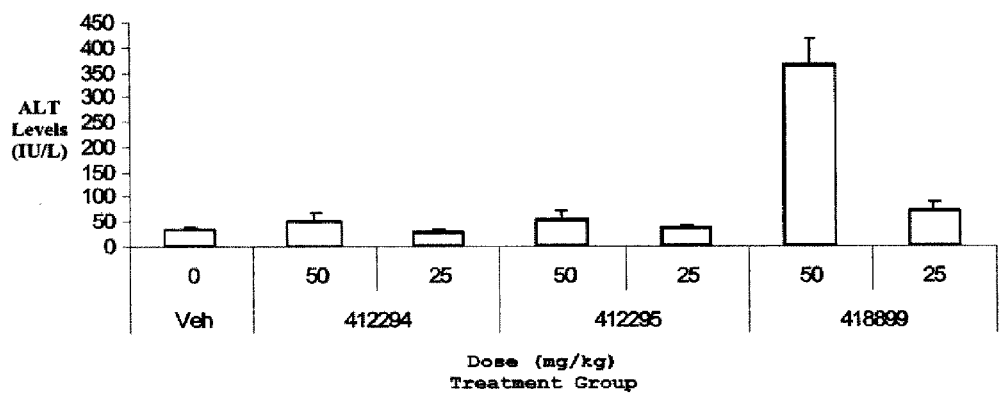
FIG. 9 provides a graphical representation of the plasma alanine aminotranferease (ALT) (FIG. 9A) and aspartate aminotransferase (AST) (FIG. 9B) levels in mice following four weeks of treatment with 25 mg/kg or 50 mg/kg antisense oligonucleotide ISIS 412294 (SEQ ID NO: 39), ISIS 412295 (SEQ ID NO: 40), or ISIS 418899 (SEQ ID NO: 166). The results show that the plasma ALT and AST levels in the mice dosed with 25 mg/kg or 50 mg/kg of ISIS 412294 (SEQ ID NO: 39) or ISIS 412295 (SEQ ID NO: 40), or dosed with 25 mg/kg of ISIS 418899 (SEQ ID NO: 166) were similar to the levels in the saline (vehicle) control group; however mice dosed with 50 mg/kg of ISIS 418899 (SEQ ID NO: 166) shows significantly increase ALT and AST levels, above the values observed in the control group.
Figure 9B:
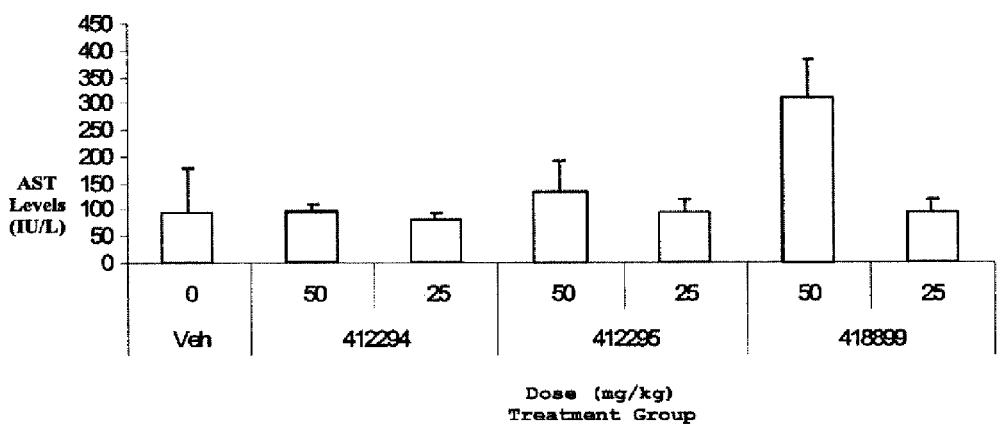

Results following 4 weeks of dosing with 25 mg/kg or 50 mg/kg antisense oligonucleotide ISIS 412294 (SEQ ID NO: 39), ISIS 412295 (SEQ ID NO: 40) or ISIS 418899 (SEQ ID NO:166) indicate a number of end-points differing significantly from the saline-treated control group of mice. These included:

1) Plasma alanine aminotranferease (ALT) and aspartate aminotransferase (AST) levels following 4 weeks of treatment with 25 mg/kg or 50 mg/kg of ISIS 412294 (SEQ ID NO: 39) or ISIS 412295 (SEQ ID NO: 40), or with 25 mg/kg of ISIS 418899 (SEQ ID NO: 166) were similar to the levels in the saline (vehicle) control, however mice dosed with 50 mg/kg of ISIS 418899 (SEQ ID NO: 166), show significantly increased ALT/AST levels above the values observed in the control group (see FIGS. 9A and 9B). This was a suprising result that was not predicted in previous studies or by the cell based assays.

Figure 10:
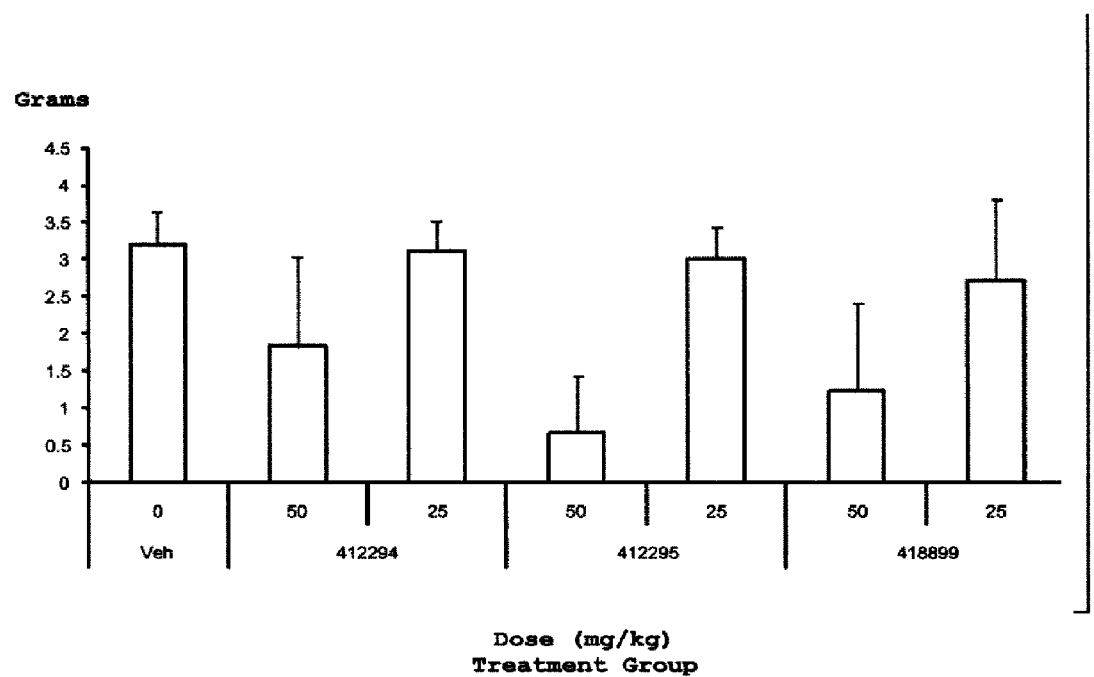
FIG. 10 provides a graphical representation of the result following four weeks of treatment with antisense oligonucleotides showing that weight gain for the 50 mg/kg 412295-treated group was significantly lower than the weight gain in the control group.

2) Weight gain for the 50 mg/kg 412295-treated group was significantly lower than the weight gain in the control group (see FIG. 10).

Conclusion

SEQ ID NO:39 (ISIS 412294) did not exhibit as many undesirable toxicological characteristics as SEQ ID NO:40 (ISIS 412295) and SEQ ID NO:166 (ISIS 418899). This result was entirely unexpected, and was not predicted by the cell culture behavior of these oligonucleotide sequences.

Example 11

Effect of a Rat CTGF Antisense Oligonucleotide (SEQ ID NO:163) on Collagen and CTGF mRNA Expression in Wounded Rats Objective CTGF antisense oligonucleotide SEQ ID NO:163 (ISIS 412442) was used to examine the ability of a CTGF antisense oligonucleotide to reduce expression both of CTGF and Col1A2 (a biomarker of scarring) in a rat animal model of scarring. This antisense oligonucleotide has an identical chemical structure as SEQ ID NO:39 (ISIS 412294), however the sequence has been modified slightly to be 100% complimentary to the rat CTGF mRNA sequence.

Wounding

Four full-thickness 0.8 centimeter biopsy punches were introduced into the backs of 10 week old hairless rats (day 1 of study), two on each side of the spinal mid-line. The wounds were left open, but dressed with a sterile occlusive bandage.

Antisense Oligonucleotide Dosing

The two biopsy sites on the right side of the animal were treated intra-dermally with the CTGF antisense oligonucleotide on Days 1, 5, 9, and 13 post-biopsy at either 3.0, 1.0, 0.3 or 0.1 mg antisense oligonucleotide. Biopsy sites on the left side of the animal were treated intra-dermally with phosphate buffer saline (PBS). The animals were sacrificed on Day 15 post-biopsy. A total volume of 200 µl of antisense oligonucleotide or PBS was delivered to each punch biopsy site. This 200 µl volume was divided into four 50 µl aliquots which were injected around the wound's periphery, at approximately 0.25 cm to 0.5 cm to the left, right, top, and bottom sides of the wound.

Sample Harvest/Sacrifice

On the sacrifice date, the animals were euthanized and a sample of skin from the center of the wound was obtained with a 0.5 cm biopsy punch, and mRNA was extracted from these samples using standard procedures. RT-PCR mRNA analysis of rat CTGF and Col1A2 was performed using the standard curve methodology for data analysis and RiboGreen as the housekeeping/normalization gene.

Results

Figure 11:
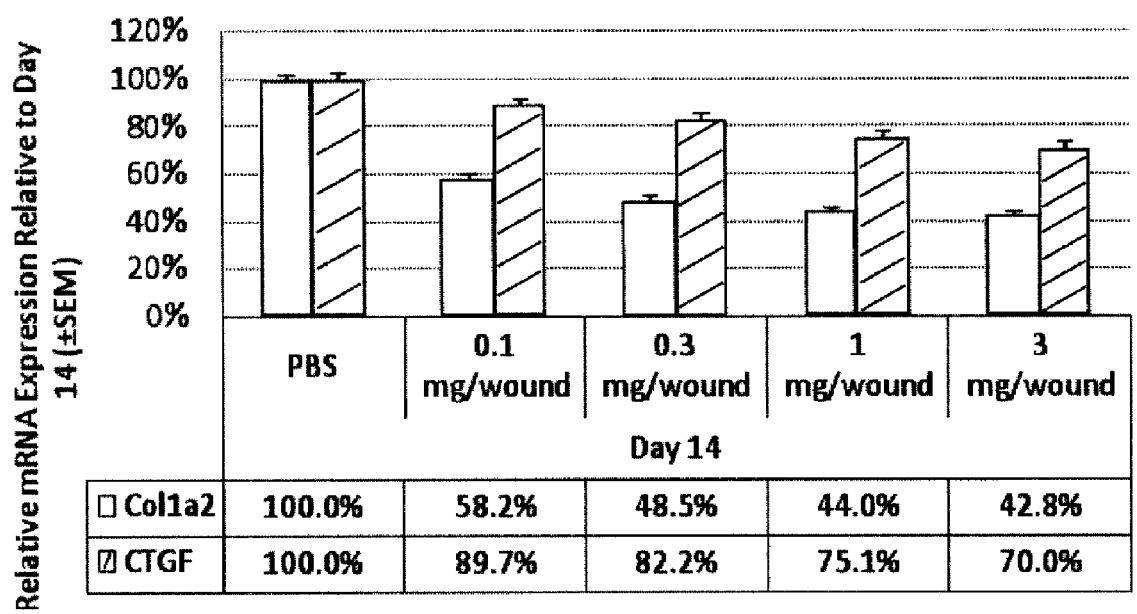
FIG. 11 shows that intradermal treatment of skin wounds in rats with 3.0, 1.0, 0.3 or 0.1 mg of CTGF antisense oligonucleotide resulted in a statistically significant reduction in both CTGF and Col1A2 mRNA expression for all doses. These results clearly demonstrate that inhibition of CTGF expression with a 2'MOE modified antisense oligonucleotide will decrease the deposition of collagen in skin.

Treatment of the rats at all doses resulted in a statistically significant reduction in both CTGF and Col1A2 mRNA expression (see FIG. 11). These results clearly demonstrate that inhibition of CTGF expression with a 2'MOE modified antisense oligonucleotide will decrease the deposition of collagen in skin, which will result in a reduction in the severity of skin scar formation.

Example 12

A Single-Dose Intra-Dermal Pharmacokinetic Study of CTGF Antisense Oligonucleotide in Rabbits Study Objective The purpose of this pharmacokinetic study in rabbit is to evaluate the concentration of a CTGF antisense oligonucleotide (SEQ ID NO:39, ISIS 412294) in rabbit skin at different times subsequent to a single intra-dermal injection.

Study Design

On day 0 of the study all animals were dosed intra-dermally (ID) with a single 100 µL injection of CTGF antisense oligonucleotide SEQ ID NO:39 at a concentration of 50 mg/mL (5 mg total dose). The animals were dosed with the antisense oligonucleotide in a site to the left of the spinal mid-line, roughly parallel to the rabbit's shoulders. The needle was inserted so that the test material was injected down towards the base of the animal's body. On days 1, 3, 7 or 14, the rabbits were euthanized and two full-thickness 1.0 cm punch biopsies were obtained, one centered over the original injection site and the other vertically below spaced 0.5 cm apart. The samples were snap frozen and stored at −80° C. prior to analysis of the antisense oligonucleotide drug levels. Results represent the mean antisense oligonucleotide levels from both biopsies at the indicated time.

Results and Conclusions

Figure 12:
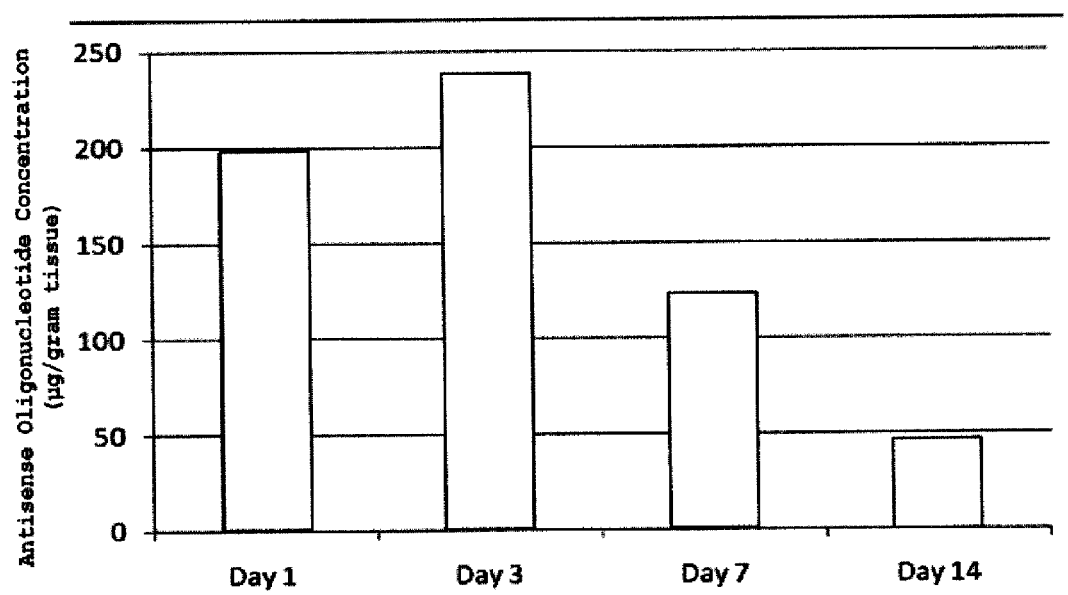
FIG. 12 provides a graphical representation showing significant levels of the CTGF antisense oligonucleotide present up to at least day 14 after 50 mg/mL (5 mg total dose) intradermal dosing in rabbits.

Significant levels of the antisense oligonucleotide are present up to at least day 14 after intradermal dosing (see FIG. 12). Therapeutic concentrations of drug are between 1 and 100 µg/gram tissues. These results demonstrated that for the first time there is a prolonged residence time of a 2'MOE antisense oligonucleotide with this chemical configuration in skin, and these results clearly show the therapeutic potential of this class of compound in skin.

Example 13

Genome Search

The potential for SEQ ID NO:39 to induce unwanted antisense effects that could translate into "off-target" toxicity was assessed by conducting a search of the human genome database for sequences that have complete or partial homology or complimentarily with the SEQ ID NO:39 nucleotide sequence.

A comprehensive search of published human DNA sequence databases was conducted to evaluate whether sequences that comprise SEQ ID NO:39 have sufficient homology with the known array of human genes, such that unwanted antisense or other inhibitory activity could be exerted against expression of human gene products other than the target CTGF (connective tissue growth factor) and thereby induce "off-target" effects. The search entailed screening for homologous sequences ranging from 20 nucleotides (i.e., the full length of SEQ ID NO:39 down to 12 nucleotides.

No off-target sites were detected in the human genome with 20, or 18 bases of homology with SEQ ID NO:39. The complete absence of off-target sites with 18, 19 or 20 bases indicates that the likelihood of any consequential off-target activity is minimal. Three 17-base homologies with SEQ ID NO:39 were identified. One of these is within the intron of the LRFN2 gene. Introns are typically spliced out of the transcript before the mRNA arrives in the cytoplasm, the site of action of SEQ ID NO:39. For this reason, SEQ ID NO:39 is not expected to affect LRFN2 expression. The two other 17-base homologies are located within inter-gene spacer regions. Inter-gene spacers are generally not transcribed but exist as double-stranded DNA in the nuclear compartment, separate from the site of action of SEQ ID NO:39. Hence, there were no 17-base homologies of concern.

Among the 16-base, 15-base and 14-base homologies found, only one was located within a known or suspected transcript (i.e., FRMD5, which encodes a lipid biosynthesis transferase active in the liver). However, the 14-base SEQ ID NO:39 homology with an mRNA sense transcript would not be conducive to antisense activity (i.e., hybridization would only be possible if a portion of the SEQ ID NO:39 sequence was complementary, not homologous, to the mRNA transcript sequence). Therefore, SEQ ID NO:39 will not affect this transcript. All other 16-base through 14-base homologies corresponded to introns or inter-gene spacers with no overlapping transcripts, predicted transcripts or expressed sequence tags. There were no 13-base homologies. Any transcripts based on only 12-nucleotide homology or shorter would present a thermodynamically unfavorable target, compared to the binding of a 20-base oligonucleotide like SEQ ID NO:39 with its intended target. Therefore, 12-base and shorter homologies do not present a significant potential for off-target antisense activity.

Therefore, the human genome database search showed that SEQ ID NO:39 has a high degree of specificity for the intended target with minimal potential for off-target effects.

Example 14

A Phase 1 Single-Dose Intra-Dermal Clinical Study to Assess the Safety and Tolerability of a CTGF Antisense Oligonucleotide (SEQ ID NO:39)

Study Objectives

The human CTGF antisense oligonucleotide SEQ ID NO:39 (Isis No. 412294) was administered to six patients by intra-dermal dosing (80 mg total dose) as part of a Phase 1 study protocol to assess the safety and tolerability of a single dose of drug.

Results

No adverse events were reported other than local injection site reactions such as erythema, inflammation, itching, and induration. The adverse events listed were reported in approximately 50% of the subjects at a severity level of "minimal". No changes were noted in serum chemistry, hematology, urinalysis, ECGs, vital signs, physical exams, and complement activation.

Conclusions

The administration of the CTGF antisense oligonucleotide at doses anticipated to be within the therapeutic range is well tolerated in humans, demonstrating the safety of this compound for treating skin scarring.

Example 15

Antisense Oligonucleotide SEQ ID NO:39 Drug Levels in Human Skin Following Intra-Dermal Dosing Skin drug levels were evaluated in a cohort of patients in an initial clinical study, where 5 patients each received 40 mg of the antisense oligonucleotide (ASO) (administered as 10 equal doses of 4 mg each). Skin biopsies were obtained 21 days following the single-dose administration of the ASO on Day 1, at the site of the simulated surgical wound (drawn line on skin as a reference for dosing locations). The punch biopsy consisted of a 4-mm cylindrical core of tissue sample. Levels of the ASO were determined using capillary electrophoresis and fluorescently-labeled sequence-specific probes and were 84.2 µg/gram of tissue. Projected therapeutic concentrations of the ASO drug are anticipated to be between 1 and 100 µg/gram tissues.

These results demonstrated that for the first time there is a prolonged residence time of a 2'MOE antisense oligonucleotide with this chemical configuration in human skin after intradermal administration, and these results clearly show the therapeutic potential of this class of compound in skin.

Example 16

A Phase 2 Randomized, Double-Blind, Within-Subject Controlled Clinical Efficacy and Safety Study of SEQ ID NO:39 on Reducing Scar Severity in Subjects Undergoing an Elective Abdominoplasty This study is a randomized, double-blind, within-subject controlled study evaluating efficacy and safety of CTGF antisense oligonucleotide SEQ ID NO:39 (i.e. the drug product). The drug product is administered adjacent to both sides of the abdominoplasty incision via intradermal injections in subjects undergoing an elective abdominoplasty.

A section of the abdominoplasty incision on either side of the midline, just lateral to the pubic hair, is treated with drug product or placebo, after the surgical incision is closed.

The study duration is approximately 24 weeks. Subjects receive the abdominoplasty on Day 1, followed by dosing of the drug product and placebo over a 10 week period. Scar observation and assessment are performed every 4 weeks up to week 12, and again at week 24.

Efficacy is determined by ratings of each matched pair of incisions.

Efficacy is evaluated at weeks 12 and 24 following the abdominoplasty surgery using the following two methods of rating severity of incisional scars:

Expert panel assessment of blinded photographs using visual analog scale (VAS);
Investigator Scar Assessment Scale Subject Scar Assessment Scale;
SEQ ID NO:39 is efficacious by these criteria.

Example 17

A Phase 2 Randomized, Double-Blind, Within-Subject Controlled Clinical Efficacy and Safety Study of SEQ ID NO:39 in Reducing Skin Scarring in Subjects Undergoing an Elective Revision of Medial Scars Resulting from Prior Breast Reduction or Mastopexy Surgery This study is a randomized, double-blind, within-subject controlled study evaluating efficacy and safety of CTGF antisense oligonucleotide SEQ ID NO:39 (i.e. the drug product). The drug product is administered to the medial portion of the revised breast reduction scars via intradermal injections. A section of either side of the medial portion of the revised breast wound/scar is treated with drug product or placebo, after the surgical incision is closed.

Up to 40 subjects are recruited into this study. The study duration is approximately 24 weeks. The subjects receive the scar revisions on Day 1, followed by drug product and placebo dosing over a 10-week period. Scar observation and assessment are performed every 4 weeks up to week 12, and again at week 24.

Efficacy is determined by ratings each matched pair of incisions. Efficacy is evaluated at weeks 12 and 24 following revision of the medial portions of the breast reduction scar using two methods of rating severity of incisional scars:

Expert panel assessment of blinded photographs using visual analog scale (VAS);
Investigator Scar Assessment Scale Subject Scar Assessment Scale
SEQ ID NO:39 is efficacious by these criteria.

---

What is claimed is:

1. A method of treating hypertrophic scarring, comprising administering to a subject in need of treatment for hypertrophic scarring a therapeutically effective amount of a composition comprising a compound which comprises a modified oligonucleotide consisting of 12-30 linked nucleosides, at least a 12 nucleobase sequence portion of which is present within the nucleobase sequence set forth in SEQ ID NO: 39, wherein the modified oligonucleotide comprises:

(a) a gap segment consisting of linked deoxynucleosides;
(b) a 5' wing segment consisting of linked modified nucleosides; and
(c) a 3' wing segment consisting of linked modified nucleosides;

wherein the gap segment is positioned between the 5 wing segment and the 3' wing segment, and wherein each modified nucleoside within each wing segment comprises a modified sugar.

2. The method of claim 1, wherein the modified oligonucleotide comprises:

(a) a gap segment consisting of thirteen linked deoxynucleosides;
(b) a 5' wing segment consisting of two linked modified nucleosides; and
(c) a 3' wing segment consisting of five linked modified nucleosides;

wherein the gap segment is positioned between the 5' wing segment and the 3' wing segment, wherein each modified nucleoside within each wing segment comprises a 2'-O-methoxyethyl sugar; and wherein each internucleoside linkage is a phosphothioate linkage.

3. The method of claim 1, wherein in the modified oligonucleotide at least one internucleoside linkage is modified.

4. The method of claim 3, wherein each modified internucleoside linkage is a phosphorothioate linkage.

5. The method of claim 3, wherein each of the remaining internucleoside linkages is a phosphodiester linkage.

6. The method of claim 4, wherein each of the internucleoside linkages is a phosphorothioate linkage.

7. The method of claim 1, wherein in the modified oligonucleotide the modified sugar is a 2'-O-methoxyethyl sugar.

8. The method of claim 1, wherein in the modified oligonucleotide at least one nucleobase is modified.

9. The method of claim 1, wherein in the modified oligonucleotide at least one cytosine nucleobase is modified.

10. The method of claim 9, wherein each modified cytosine nucleobase is a 5'-methylcytosine.

11. The method of claim 10, wherein each cytosine within the nucleobase sequence of said modified oligonucleotide is a 5'-methylcytosine.

12. The method of claim 1, wherein said composition is administered topically.

13. The method of claim 1, wherein said composition is administered subcutaneously.

14. The method of claim 1, wherein said composition is administered intradermally.

15. The method of claim 1, wherein said composition is administered locally into fibrotic tissue.

16. The method of claim 1, wherein the hypertrophic scarring results from dermal wound healing.

17. The method of claim 16, wherein the wound is selected from the group consisting of skin breakage, surgical incision and burn.

18. The method of claim 1, wherein after treatment said subject experiences an improvement in scar severity at least by an amount selected from the group consisting of 15%, 20%, 25%, 30%, 35%, 40%, 45%, 50%, 55%, 60%, 65%, 70%, 75%, 80%, 85%, 90%, 95% and 99%.

19. A method of treating hypertrophic scarring, comprising administering to a subject in need of treatment for hypertrophic scarring a therapeutically effective amount of a composition comprising a compound which comprises a modified oligonucleotide consisting of 20 linked nucleosides having a nucleobase sequence as recited in SEQ ID NO 39, wherein the modified oligonucleotide comprises:
 (a) a gap segment consisting of thirteen linked deoxynucleosides;
 (b) a 5' wing segment consisting of two linked modified nucleosides; and
 (c) a 3' wing segment consisting of five linked modified nucleosides;
 wherein the gap segment is positioned between the 5' wing segment and the 3' wing segment,
 wherein each modified nucleoside within each wing segment comprises a 2'-O-methoxyethyl sugar,
 wherein each internucleoside linkage is a phosphorothioate linkage, and
 wherein each cytosine nucleobase is a 5'-methylcytosine.

20. A method of treating hypertrophic scarring, comprising administering to a subject in need of treatment for hypertrophic scarring a therapeutically effective amount of a composition comprising an antisense oligonucleotide consisting of the nucleotide sequence of SEQ ID NO:39, said antisense oligonucleotide further characterized as having, from 5' to 3' direction,
 a 5' wing segment consisting of two nucleotides, a gap segment consisting of 13 nucleotides, and a 3' wing segment consisting of five nucleotides,
 wherein each nucleotide of said 5' and 3' wing segments comprises a 2'-O-methoxyethyl sugar,
 wherein each nucleotide of said gap segment comprises a deoxyribose sugar,
 wherein each cytosine base of said antisense oligonucleotide is a 5'-methylcytosine, and
 wherein the internucleotide linkages between each nucleotide of said antisense oligonucleotide are phosphorothioate linkages.

21. The method of claim 20, wherein said composition is administered topically.

22. The method of claim 20, wherein said composition is administered subcutaneously.

23. The method of claim 20, wherein said composition is administered intradermally.

24. The method of claim 20, wherein said composition is administered locally into fibrotic tissue.

25. The method of claim 20, wherein the hypertrophic scarring results from dermal wound healing.

26. The method of claim 25, wherein the wound is selected from the group consisting of skin breakage, surgical incision and burn.

27. The method of claim 20, wherein after treatment said subject experiences an improvement in scar severity at least by an amount selected from the group consisting of 15%, 20%, 25%, 30%, 35%, 40%, 45%, 50%, 55%, 60%, 65%, 70%, 75%, 80%, 85%, 90%, 95% and 99%.

* * * * *